US010408786B2

(12) United States Patent
Kuhr et al.

(10) Patent No.: US 10,408,786 B2
(45) Date of Patent: Sep. 10, 2019

(54) DISTRIBUTABLE CHEMICAL SAMPLING AND SENSING SYSTEM

(71) Applicant: ChemiSensor, LLP, Monument, CO (US)

(72) Inventors: Werner G. Kuhr, Hoboken, NJ (US); Craig Rhodine, Monument, CO (US)

(73) Assignee: Chemisensor, LLP, Monument, CO (US)

( * ) Notice: Subject to any disclaimer, the term of this patent is extended or adjusted under 35 U.S.C. 154(b) by 171 days.

(21) Appl. No.: 15/616,870

(22) Filed: Jun. 7, 2017

(65) Prior Publication Data

US 2017/0336341 A1    Nov. 23, 2017

Related U.S. Application Data

(63) Continuation-in-part of application No. 13/795,318, filed on Mar. 12, 2013, now abandoned.

(60) Provisional application No. 61/659,873, filed on Jun. 14, 2012.

(51) Int. Cl.
| | |
|---|---|
| *G01N 27/407* | (2006.01) |
| *G01N 1/22* | (2006.01) |
| *G01N 30/64* | (2006.01) |
| *G01N 33/02* | (2006.01) |
| *G01N 30/72* | (2006.01) |
| *G01N 30/88* | (2006.01) |
| *G01N 27/48* | (2006.01) |
| *G01N 1/40* | (2006.01) |

(52) U.S. Cl.
CPC ............ *G01N 27/407* (2013.01); *G01N 1/22* (2013.01); *G01N 1/2214* (2013.01); *G01N 1/405* (2013.01); *G01N 1/4022* (2013.01); *G01N 27/48* (2013.01); *G01N 30/64* (2013.01); *G01N 30/7206* (2013.01); *G01N 30/88* (2013.01); *G01N 33/02* (2013.01); *G01N 2030/8809* (2013.01)

(58) Field of Classification Search
CPC .......... G01N 33/0036; G01N 33/0047; G01N 33/0009; G01N 33/497; G01N 1/2214; G01N 1/405; G01N 1/22; G01N 2033/4975; G01N 27/407; G01N 27/4074; G01N 27/4078
See application file for complete search history.

(56) References Cited

U.S. PATENT DOCUMENTS

| | | | |
|---|---|---|---|
| 4,438,207 A | 3/1984 | Fahrenholtz | |
| 4,833,073 A | 5/1989 | McNally | |
| 5,124,267 A | 6/1992 | Humpel | |
| 5,144,030 A | 9/1992 | Wang | |
| 5,219,747 A | 6/1993 | McNally | |
| 5,264,373 A | 11/1993 | Wang | |
| 5,302,703 A | 4/1994 | Buechler | |
| 5,426,056 A | 6/1995 | Nacson | |
| 5,463,027 A | 10/1995 | Wang | |
| 5,656,142 A * | 8/1997 | Park | C12Q 1/002 204/403.1 |
| 5,726,435 A | 3/1998 | Hara | |
| 5,817,766 A | 10/1998 | Hui | |
| 5,910,419 A | 6/1999 | Johnson | |
| 6,095,153 A | 8/2000 | Kessler | |
| 6,146,895 A | 11/2000 | Green | |
| 6,605,444 B1 | 8/2003 | Klein | |
| 6,686,209 B2 | 2/2004 | Wang | |
| 6,761,164 B2 | 7/2004 | Amirpour | |
| 6,772,756 B2 | 8/2004 | Shayan | |
| 6,990,978 B2 | 1/2006 | Shayan | |
| 7,550,112 B2 | 6/2009 | Gou | |
| 7,564,027 B2 | 7/2009 | Finch | |
| 7,624,734 B2 | 12/2009 | Balch | |
| 7,749,772 B1 | 7/2010 | Wang | |
| 7,776,618 B2 | 8/2010 | Nazareth | |
| 7,790,400 B2 | 9/2010 | Jehanli | |
| 7,816,143 B2 | 10/2010 | Day | |
| 7,878,416 B2 | 2/2011 | Lapstun | |

(Continued)

FOREIGN PATENT DOCUMENTS

| | | |
|---|---|---|
| EP | 0736529 | 10/1996 |
| WO | WO2005066618 | 7/2005 |
| WO | WO2006134386 | 12/2006 |

OTHER PUBLICATIONS

Lowe, Eleanor R. et al. "Indirect detection of substituted phenols and cannabis based on the electrochemical adaption of the Gibbs reaction." Analytical and Bioanalytical Chemistry (2005) 383 523-531. (Year: 2005).*

(Continued)

*Primary Examiner* — Christopher Adam Hixson
(74) *Attorney, Agent, or Firm* — Werschulz Patent Law, LLC; Patricia P. Werschulz, Esq.

(57) ABSTRACT

A distributable sampling and sensing instrument for chemical analysis of consumable foods and other agricultural products. The distributable sampling system is used to separate and concentrate the chemicals of interest obtained from samples at remote locations via thermal desorption onto a detachable target substrate that can be analyzed on-site or off-site. The volatile components adsorbed onto the target substrate can be analyzed with specific sensors (e.g., electrochemical sensors) or the assembly can be sent to a central lab and analyzed with conventional chemical instrumentation (e.g., GC-MS). This instrument provides the capability to enable chemical analysis of a wide range of chemical species of interest in a wide range of environments and conditions.

7 Claims, 15 Drawing Sheets

(56) References Cited

U.S. PATENT DOCUMENTS

| | | | |
|---|---|---|---|
| 8,071,394 | B2 | 12/2011 | Wu |
| 8,160,671 | B2 | 4/2012 | Kamath |
| 2004/0147767 | A1 | 7/2004 | Whittle |
| 2005/0183582 | A1 | 8/2005 | McFadden |
| 2006/0281189 | A1 | 12/2006 | Minter |
| 2007/0163327 | A1 | 7/2007 | Mansson |
| 2009/0088336 | A1 | 4/2009 | Burd |
| 2009/0294298 | A1 | 12/2009 | Compton |

OTHER PUBLICATIONS

Musshoff, Frank et al. "Fully automated determination of cannadinoids in hair samples using headspace solid-phase microextraction and GC-MS." Journal of Analytical Toxicology (2002) 26 554-560.

Musshoff, Frank et al. "Automated headspace solid-phase dynamic extraction for the determination of cannabinoids in hair samples." Forensic Science International (2003) 133 32-38.

Fakhari, Ali Reza et al. "A new method based on headspace adsorptive accumulation using a carbozylated multi-walled carbon nanotubes modified electrode: application for trace determination of nitrobenzene and nitrotoluene in water and wastewater." Analytical Methods (2011) 3 2593-2598.

B. Gilbert-Lopez, J_ F. Garcia-Reyes and A. Molina-Diaz, "Sample treatment and determination of pesticide residues in fatty vegetable matrices: A review," TALANTA, vol. 79, No. 2, pp. 109-128, 2009.

M. LeDoux, "Analytical methods applied to the determination of pesticide residues in foods of animal origin. A review of the past two decades," Journal of Chromatography A, vol. 1281, No. 8, pp. 1021-1036, 2011.

K. Ridgway, S. P. D. Lalljie and R. M. Smith, "Sample preparation techniques for the determination of trace residues and contaminants in foods," Journal of Chromatography A, vol. 1153, pp. 36-53, 2007.

P. Zollner, A. Leitner, D. Berner, M. Kleinova, J_ Jodlbauer, B. Mayer and W. Lindner, "Improving LC-MS/MS analyses in complex food matrices, Part I—Sample preparation and chromatography," LC GC Europe, vol. 16, No. 3, p. 163, 2003.

C. Ferrer, M. Gomez, J_ Garcia-Reyes, I. Ferrer, E. Thurman and A. Fernandez-Alba, "Determination of pesticide residues in olives and olive oil by matrix solid-phase dispersion followed by gas chromatography/mass spectrometry and liquid chromatography/tandem mass spectrometry," Journal of Chromatography A, vol. 1069, No. 2, pp. 183-194, 2005.

F. Calbiani, M. Careri, L. Elviri, A. Mangia, L. Pistara and I. Zagnoni, "Development and in-house validation of a liquid chromatography-electrospray-tandem mass spectrometry method for the simultaneous determination of Sudan I, Sudan II, Sudan III and Sudan IV in hot chilli products," Journal of Chromatography A, vol. 1042, pp. 123-130, 2004.

J_ Hajslova and J_ Zrostlikova, "Matrix effects in (ultra)trace analysis of pesticide residues in food and biotic matrices," Journal of Chromatography A, vol. 1000, pp. 181-197, 2003.

H. Aramaki, "Forensic chemical study on Marihuana 1. A detection method of the principal constituents by thin-layer and gas chromatography," Chemical and Pharmacological Bulletin, vol. 16, No. 5, pp. 822-826, 1968.

T.B. Vree, D.D. Breiner, C.A.M. van Ginnekan and J.M. van Rossum, "Identification in Hasish of THC, cannabinol and cannabinol analogues with a methyl side chain," Journal of Pharmacy and Pharmacology, vol. 24, No. 1, pp. 7-12, 1972.

R. A. de Zeeuw, T. M. Malingre and F. Merkus, "II-1-Tetrahydrocannabinolic acid, an important component in the evaluation of cannabis products," Journal of Pharmacy and Pharmacology, vol. 24, No. 1, pp. 1-6, 1972.

M. R. Paris and R. R. Paris, "Importance de la chromatographic pour l'etude des constituents du *cannabis saliva* L.," Bulletin de la Societe chimique de France, vol. 1, pp. 118-122, 1973.

C. E. Hadley and K. Turner, "Constituents of *Cannabis saliva* L. 11: Absence of cannabidiol in an African variant," Journal of Pharmaceutical Sciences, vol. 62, No. 2, pp. 251-255, 1973.

S. N. Sharma and J_ D. Tewari, "Separation and identification of cannabinoids from *Cannabis indica* L. by thin-layer chromatography," Pharmazie, vol. 34, No. 1, pp. 54-55, 1979.

P. Oroszlan, "Separation, quantitation and isolation of cannabinoids from Cannabis saliva by overpressure layer chromatography," Journal of Chromatography, vol. 388, No. 1, pp. 217-224, 1987.

P. B. Baker, "Determination of the distribution of cannabinoids in cannabis resin using high-performance liquid chromatography," Journal of Analytical Toxicology, vol. 4, pp. 145-152, 1980.

C. G. Vaughan and R. N. Smith, "High-pressure liquid chromatography of cannabis: quantitative analysis of acidic and neutral cannabinoids," Journal of Chromatography, vol. 129, pp. 347-354, 1976.

S. L. Kanter, M. R. Musumeci and L. E. Hollister, "Quantitative determination of II-9-Tetrahydrocannabinol and II-/9-tetrahydrocannabinolic acid in marihuana by high-pressure liquid chromatography," Journal of Chromatography, vol. 171, pp. 504-508, 1979.

D. J_ Harvey, "Chemistry, metabolism and pharmacokinetics of the cannabinoids," in Marihuana in Science and Medicine, New York, Raven Press, 1984, pp. 37-107.

SL. Kanter, M.R. Musumeci, LE.Hollister, Quantitative Determination of D-9-THC and D-9-THC acid in marihuana by high performance liquid chromatography, J_ Chromatography, vol. 171, pp. 504-508, 1979.

I. Centini et al., "Packed-column chromatography, high-resolution gas chromatography and high-pressure liquid chromatography in comparison for the analysis of cannabis constituent," Forensic Science International, vol. 21, No. 2, pp. 129-137, 1983.

I. Nakahara, "Studies on confirmation of cannabis use. I. Determination of the cannabinoid contents in marijuana cigarette, tar, and ash using high-performance liquid chromatography with electrochemical detection," Journal of Analytical Toxicology, vol. 9, No. 3, pp. 121-124, 1985.

T. B. Vree, "Gas chromatography of cannabis constituents and their synthetic derivatives," Journal of Chromatography, vol. 74, pp. 209-224, 1972.

M. Novotny et al., "Analysis of marijuana samples from different origins by high resolution gas-liquid chromatography for forensic application," Analytical Chemistry, vol. 48, No. 1, pp. 24-29, 1976.

L. Stromberg, "Minor components of cannabis resin. VI. Mass spectrometric data and gas chromatographic retention times of components eluted after cannabinol," Journal of Chromatography, vol. 121, pp. 313-322, 1976.

D. J_ Harvey, "Comparison of fourteen substituted silyl derivatives for the characterization of alcohols, steroids and cannabinoids by combined gas-liquid chromatography and mass spectrometry," Journal of Chromatography, vol. 147, pp. 291-298, 1978.

H. Spiteller and G. Grote, "Neue cannabinoide. II," Journal of Chromatography, vol. 154, pp. 13-23, 1978.

T.R. Raharjo and R. Verpoorte, "Methods for the Analysis of Cannabinoids in Biological Materials: A Review," Phytochemical Analysis, vol. 15, pp. 79-94, 2004.

C. Arthur and J_ Pawliszyn, Solid phase microextraction with thermal desorption using fused silica optical fibers, Anal Chem, vol. 62, pp. 2145-2148, 1990.

H. Kataoka, H. Lord and J_ Pawliszyn, Applications of solid-phase microextraction in food analysis, Journal of Chromatography A, vol. 880, p. 35-62, 2000.

R. Smith, "High-pressure liquid chromatography of cannabis identification of separated constituents.," J_ Chromatogr., vol. 115, pp. 101-106, 1975.

S. Kanter, M. Musumeci and L. Hollister, "Quantitative determination of D9-tetrahydrocannabinol and D9-tetrahydrocannabinolic acid in marihuana by high pressure liquid chromatography," J Chromatogr, vol. 171, p. 504-508, 1979.

J_ Turner and P. Mahlberg, "Effects of sample treatment on chromatographic analysis of cannabinoids in *Cannabis saliva* L. (Cannabaceae)," J_ Chromatogr., vol. 283, p. 165-171, 1984.

T. Veress, J_ Szanto and L. Leisztner, "Determination of cannabinoid acids by high-performance liquid chromatography of their

(56) References Cited

OTHER PUBLICATIONS neutral derivatives formed by thermal decarboxylation process in an open reactor," J. Chromatogr., vol. 520, p. 339-347, 1990.

J. Parker and B. Stembal, "Review of gas-liquid chromatography of marihuana," JAOAC, vol. 57, p. 888-892, 1974.

D.W. Lachenmeier, L. Kroener, F. Musshoff and B. Madea, "Determination of cannabinoids in hemp food products by use of headspace solid-phase microextraction and GC-MS," Anal. Bioanal. Chem. vol. 378, pp. 183-189, 2004.

G. Thakur, R. Duclos Jr. and A. . Makriyannis, Natural cannabinoids: templates for drug discovery, Life Sci, vol. 78, p. 454-466, 2005.

K. Mechtler, J. Bailer, K. de Hueber, "variations of D-9-THC content in single plants of hemp varieties," Industrial Crops and Products, vol. 19, pp. 19-24.

K. Hillig and P. Mahlberg, A chemotaxonomic analysis of cannabinoid variation in Cannabis (Cannabaceae), Am. J. Bot., vol. 91, p. 966, 2004.

N. Doorenbos, P. Fetterman, M. Quimby and C. Turner, Cultivation, extraction, and analysis of *Cannabis saliva* L., Annals of the New York Academy of Sciences vol. 191, pp. 3-14. 1971.

A. Stalker, J. van Schoonhoven, A. de Vries, I. Bobeldijk-Pastorova, W. Vaes and R. van den Berg, Determination of cannabinoids in cannabis products using liquid chromatography-ion trap mass spectrometry, J. Chromatogr. A, vol. 1058, p. 143-151, 2004.

E. R. Lowe, R. G. Compton and C. E. Banks, "Indirect detection of substituted phenols and cannabis based on the electrochemical adaptation of the Gibbs reaction," Anal Bioanal Chem, vol. 383, p. 523-531, 2005.

P. Josephy and A. Damme, Reaction of Gibbs reagent with para-substituted phenols, Anal Chem, vol. 56, p. 813-814, 1984.

N. Craft, G. Byrd and L. Hilpert, Preparation and certification of standard reference material 1507: 11-nor-.DELTA.9-tetrahydrocannabinol-9-carboxylic acid in freeze-dried urine ,Anal Chem, vol. 61, p. 540-44, 1989.

A. Goodwin, C. E. Banks and R. G. Compton, "Graphite Micropowder Modified with 4-Amino-2,6-diphenylphenol Supported on Basal Plane Pyrolytic Graphite Electrodes: MicroSensing Platforms for the Indirect Electrochemical Detection of D9-Tetrahydrocannabinol in Saliva," Electroanalysis, vol. 18, No. 11, pp. 1063-1067, 2006.

C. Moore, A. Negrusz and D. Lewis, "Determination of drugs of abuse in meconium," J Chromatogr B, vol. 713, p. 137-146, 1998.

I. Breindah and K. Andreasen, "Determination of 11-nor-DELTA9-tetrahydro-cannabinol-9-carboxylic acid in urine using HPLC and electrospray ionisation mass spectrometry," J Chromatogr B, vol. 732, pp. 155-164, 1999.

M. Weaver, B. Gan, E. Allen, L. Baugh, F. Liao, R. Liu, J. Langner, A. Walia and L. Cook, "Correlations on radioimmunoassay, fluorescence polarization immunoassay and enzyme immunoassay of cannabis metabolites with gas chromatography/ mass spectrometry analysis of 11-nor-D9-tetrahydrocannabinol-9-carboxylic acid in urine specimens.," Forensic Sci Int, vol. 49, p. 43-56, 1991.

M. Bacigalupo, A. Ius, G. Meroni, G. Grassi and A. Moschella, "Time-resolved fluoro-immunoassay for D9-tetrahydrocannabinol as applied to early discrimination of Cannabis sativa plants.," J Agric Food Chem, vol. 47, p. 2743-45, 1999.

J. Ngeh-Ngwainbi, P. H. Foley, Shia S. Kuan, G. G. Guilbault, Parathion antibodies on piezoelectric crystals, J. Am. Chem. Soc., vol. 108, pp. 5444-5447, 1986.

B. S. Yu et al., "Electrochemical oxidation of phenol on metal oxide electrodes.," Journal of Water Chemistry and Technology, vol. 34, No. 1, pp. 24-27, 2012.

* cited by examiner

DISTRIBUTABLE CHEMICAL SAMPLING AND SENSING SYSTEM

CROSS-REFERENCE TO RELATED APPLICATIONS

This application is a continuation-in-part nonprovisional utility application of the nonprovisional patent application Ser. No. 13/795,318 filed in the United States Patent Office on Mar. 12, 2013, and claims the priority thereof and is expressly incorporated herein by reference in its entirety; patent application Ser. No. 13/795,318 is the nonprovisional patent application of the provisional patent application, Ser. No. 61/659,873, filed in the United States Patent Office on Jun. 14, 2012 and claims the priority thereof and is expressly incorporated herein by reference in its entirety.

TECHNICAL FIELD

The present disclosure relates generally to chemical analysis of food and agricultural products. More particularly, the present disclosure relates to instrumentation used in the collection of chemical samples from food and agricultural products, the chemical analysis of those samples and the disposition of the data collected in the chemical analysis of those samples.

BACKGROUND

There has been a dramatic increase in the need for the chemical analysis of food and agricultural products in recent years. This comes as a result of many factors, some which include increased use of pesticides and fungicides (especially in the developing world), increased regulation and taxation by local and federal governments as well as increased concern about contamination and adulteration of food products. Pest control in intensive agriculture involves treatment of crops (fruits, vegetables, cereals, etc.) pre- and post-harvests with a variety of synthetic chemicals generically known as pesticides. The resurgence of 'organic' foods in the last decade has spurred a closer examination of the pesticide and herbicide content of foods consumed. 'Organic' is a labeling term that refers to agricultural products produced in accordance with Organic Foods Production Act and the National Organic Program (NOP) Regulations. The principal guidelines for organic production are to use materials and practices that enhance the ecological balance of natural systems and that integrate the parts of the farming system into an ecological whole. Organic agriculture practices cannot ensure that products are completely free of residues; however, methods are used to minimize pollution from air, soil and water.

Herbicides and insecticides are mainly used in the pre-harvest stages, rodenticides are employed in the post-harvest storage stages, and fungicides are applied at any stage of the process depending on the crop. These chemicals can be transferred from plants to animals via the food chain. For example, more than 800 different kinds of pesticides are used for the control of insects, rodents, fungi and unwanted plants in the process of agricultural production. Although most of these are meant to degrade in soil, water and atmosphere before the food product reaches the consumer's table, trace amounts of these pesticide residues can be transferred to humans via the food chain, being potentially harmful to human health [1].

To limit the acceptable risk levels of pesticide residues, federal regulations on maximum residue limits (MRLs) for pesticide residues in foods have been established in many countries and health organizations, for example in the United States, Japan, European Union, and Food and Agriculture Organization (FAO). They are set for a wide range of food commodities of plant and animal origin, and they usually apply to the product as placed on the market. MRLs are not simply set as toxicological threshold levels, they are derived after a comprehensive assessment of the properties of the active substance and the residue behavior on treated crops. These legislative limits have become stricter than ever due to the concerns of food safety and the demands of trade barriers, driving the demand for more sensitive and reliable chemical analysis methods for pesticide residues [2].

The chemical analysis of these residues in foods currently requires both extensive sample preparation and expensive analytical instrumentation. Most pesticide residue detection methods for food samples comprise two key preparation steps prior to identification/quantification: extraction of target analytes from the bulk of the matrix, and partitioning of the residues in an immiscible solvent and/or clean-up of analytes from matrix co-extractives, especially fat which interferes with assays. Although there has been significant advancement in the sophistication and power of analytical instruments [3], the ultimate detection limits and quantification accuracy are still primarily influenced by interferences from food matrices [4] [5] [6] [7]. Thus, sample preparation is the bottleneck for the effective and accurate chemical analysis of trace pesticide residues [4] [5].

The aim of sample preparation is to isolate the trace amounts of analytes from a large quantity of complex matrices and eliminate the interferences from the food matrix as much as possible. Typical sample preparation steps include the sampling/homogenization, extraction, and clean-up. Among them, the extraction and clean-up steps play a critical role in the success of pesticide residue chemical analysis. The traditional sample extraction methods, especially liquid-liquid extraction (LLE), have been widely used for pesticide residue chemical analysis.

However, most of these methods are time consuming and use large quantities of organic solvents to remove interference. Recent analytical developments have attempted to minimize the number of physical and chemical manipulations, the solvent volumes, the number of solvent evaporation steps, the use of toxic solvent, and have aimed to automate the extraction and clean-up procedures as far as possible. These include: supercritical-fluid extraction (SFE), pressurized-liquid extraction (PLE), microwave-assisted extraction (MAE), ultrasound-assisted extraction (UAE), gel permeation chromatography (GPC), solid-phase extraction (SPE), molecularly imprinted polymers (MIPs), matrix solid-phase dispersion (MSPD), solid-phase micro-extraction (SPME), QuEChERS, cloud point extraction (CPE) and liquid phase micro-extraction (LPME).

Analysis of Naturally Occurring Molecular Components of Agricultural Products

Another area of interest is the chemical analysis of intrinsic molecular components in food products that are regulated for economic or health reasons. Examples include alcohol in beer, liquor or spirits, caffeine in coffee, nicotine in tobacco products and cannabinoids in marijuana-based products. Rather than address all of these products, we will consider, as an example, the regulation of cannabinoids in various products. Numerous methods for identifying *Cannabis* constituents have appeared in the literature dating back to 1964 [8]. Some of these techniques were very simple, involving TLC on silica gel plates with visual detection by color reaction [9] [10] [11] [12] [13] [14]. The development of hyphenated chromatographic techniques has enabled positive identification of the major components of *Cannabis* samples. These techniques include gas chromatography with mass spectrometry, diode-array ultraviolet absorption detectors (DAD) in conjunction with high-performance liquid chromatography (HPLC), and UV/Visible wavelength scanners in conjunction with thin-layer chromatography (TLC). These techniques allow identification of the three main neutral *Cannabis* constituents (FIG. 1)—cannabidiol (CBD), Δ-9-tetrahydro-cannabinol (Δ9-THC) and cannabinol (CBN)—by comparison with published data in each area. HPLC using normal or reversed phases and detection by absorption at different wavelengths [15] [16] [17] [18] [19] [20] or electrochemical means [21], and more complex techniques combining capillary or packed-column GC with mass spectrometry [22] [23] [24] [25] [26].

Gas chromatography coupled with mass spectrometry (GCMS), seems to have emerged as the method of choice for chemical analysis of cannabinoids in hemp food products [22] [23] [24] [25] [26]. The official method of the European Community for the quantitative determination of THC in hemp varieties [27] uses gas chromatography with a flame ionization detector. On the basis of THC content *Cannabis* plants are divided into fiber-type and drug-type plants. The ratio (THC+CBN)/CBD has been proposed for distinguishing between the phenotypes of *Cannabis* plants; if the ratio obtained is greater than 1, the *Cannabis* plant is classified as drug-type; if it is less than 1, it is a fiber-type.

After the legalization of fiber-hemp cultivation in many parts of the world, hemp food products, mostly sold in esoteric stores, were eaten, because of supposed psychoactive properties associated with a potential THC content. Positive drug tests for marijuana use have been reported after ingestion of hempseed oil and other hemp foods. Since the mid 1990's, hemp food has gradually expanded into the natural product market and is increasingly found in natural food stores sold for nutritional and health benefits. A wide variety of hemp-based products is available, including hemp leaves (tea), hemp seed and seed derivatives, oil, flour, beverages (beer, lemonade), and cosmetic products. Hemp food products, even from fiber-type *Cannabis* varieties, generally contain measurable amounts of THC. Previous analyses of hemp seed oil have revealed a wide range of THC concentrations between 11.5-117.5 mg kg-1 and 7-150 mg kg-1. For sample preparation, all these methods use traditional liquid-liquid extraction (LLE), which is time-consuming and requires large volumes of solvents.

Sample Preparation

For "dirty" samples, e.g., plant materials, GC used with vaporizing injection techniques is most suitable. "Classical" hot split-less injection of a solvent extract of the plant material is the most frequently applied injection technique, however, some adverse effects such as discrimination of low volatiles, sorption and thermal degradation can occur. Another alternative to classical hot split-less injection is programmable temperature vaporization (PTV). This injection technique, first introduced in 1979, comprises injection of the sample into the cold liner (temperature held below or near the solvent boiling point) and subsequent increase of temperature and transfer of analytes. This technique was shown to avoid discrimination of low volatile compounds and avoid degradation of thermally unstable analytes. The main advantage of PTV, however, includes the possibility of large volume injection (LVI). In the solvent split mode, the PTV allows one to introduce up to 1 ml of sample into the GC system. Injection of large sample volumes not only system. Injection of large sample volumes not only enables significant improvement of overall sensitivity of the analytical method, but also makes the PTV injector applicable for the on-line coupling of GC techniques with various clean-up and enrichment techniques. Otherwise, most analytical procedures require extensive extraction and concentration enhancement steps that make the chemical analysis fairly complex.

Typical procedures used to extract neutral cannabinoids utilize solvent extraction of the plant material. The extracts are obtained by ultrasound mixing (for 15 minutes) of each of the samples, in the ratio of 100 mg of substance to 10 ml of solvent (a mixture consisting of 90 percent hexane and 10 percent chloroform), after which the extracts are ultra-centrifuged for 15 minutes at 10,000 revolutions per minute to isolate the clear supernatant. Solid-phase microextraction (SPME), discovered and developed by Pawliszyn and co-workers [28], has recently emerged as a versatile solvent-free alternative to these conventional liquid-liquid extraction procedures.

Headspace solid-phase microextraction (HS-SPME) is based on the distribution of analytes between the sample, the headspace above the sample, and a coated fused-silica fiber. Analytes are absorbed by the coating of the fiber, where they are focused, until the concentrations in the phases are in equilibrium. Subsequently, the fiber can be injected directly into a GC injection port for thermal desorption. Headspace extraction contrasts with extraction of the analytes by dipping the fiber into the aqueous phase (direct immersion, DISPME) and is advantageous because the low matrix interferences result in a diminished chromatographic background, solvent consumption is markedly reduced and its overall technical performance is fast and simple. The use of SPME in food chemical analysis was recently reviewed by Kataoka [29].

A more complete approach for the chemical analysis of all cannabinoids in plant samples uses heat to induce the decarboxylation of acidic components. Typically, neutral cannabinoids are formed during storage of the plant material but, in order to obtain total cannabinoid in the neutral form, Smith [30] heated the plant material at 100° C. for 6 min under a nitrogen purge. Later investigations showed that stronger heating for prolonged times (i.e. 200° C. for 30 min) caused loss of neutral cannabinoids by evaporation even when the samples were treated in screw cap culture tubes under an atmosphere of nitrogen [31]. Heating plant material at 37 and 60° C. gave significantly different results for neutral cannabinoids [32].

Veress et al. [33] investigated decarboxylation of cannabinoid acids in an open reactor in a study which involved different solvents (n-hexane, ethylene glycol, diethylene glycol, n-octanol, dioctyl phthalate and dimethylsulphox-ide), different temperatures and heating times, and various decarboxylation media, for example glass and various sorbent surfaces. The conclusion was that the optimum conditions for the decarboxylation of cannabinoid acids, in the presence or absence of organic solvent, always required temperatures at which the neutral cannabinoids evaporated. Consequently, it is not possible to bring about the conversion of cannabinoid acids into equivalent amounts of neutral cannabinoids by simply heating in an open reactor. It appears that the best conditions for the decarboxylation of cannabinoid acids in closed reactors (screw cap culture tubes) involve heating the samples at 200° C. for just 2 min [31].

Sample Handling and Tracking

In many cases, it is difficult to track samples, especially when the sample material is not directly connected to a sub-sample, i.e., the sample extract. In many instances, sample tracking can be facilitated through the use of Automatic Identification and Data Capture (AIDC), a term frequently used to describe the identification of articles and collection of data into a processor controlled device without the use of a keyboard. AIDC technology is designed to increase efficiency in collection and identification by reducing errors and increasing the rate of identification and collection. For the purposes of automatic identification, a product item is commonly identified by a 12-digit Universal Product Code (UPC), encoded machine-readably in the form of a printed bar code. The most common UPC numbering system incorporates a 5-digit manufacturer number and a 5-digit item number. Because of its limited precision, a UPC is used to identify a class of product rather than an individual product item. The Uniform Code Council and EAN International define and administer the UPC and related codes as subsets of the 14-digit Global Trade Item Number (GTIN).

Within supply chain management, there is considerable interest in expanding or replacing the UPC scheme to allow individual product items to be uniquely identified and thereby tracked. Individual item tagging can reduce "shrinkage" due to lost, stolen or spoiled goods, improve the efficiency of demand-driven manufacturing and supply, facilitate the profiling of product usage, and improve the customer experience.

There are two main contenders for individual item tagging: visible two-dimensional bar codes, and radio frequency identification (RFID) tags. Bar code symbols and bar codes represent one type of AIDC technology. Bar codes have become ubiquitous parts of everyday commercial transactions. Merchandise carried by grocery stores, for example, is labeled with a barcode. A scanner is used to identify an item at the point of purchase by the consumer. The scanner uses the bar code information to look up the item's price. The price is then provided to a cash register for tallying the customer's bill.

Bar codes traditionally consist of a sequence of two element types: bars and spaces. The bars and spaces are arranged such that the bars are parallel and the spaces separate the bars. One encoding methodology varies the width and the sequence of the elements to encode alphanumeric data. The particular encoding methodology is referred to as a barcode symbology. An optical scanner is used to read the bar code symbol and decode the bar code to provide the original alphanumeric data.

The use of the data may vary depending upon the needs of the inquiring entity. A grocery store, for example, may need a unique identifier for a particular product in order to enable calculation of price at checkout or for managing inventory. A medical supplier, however, may need to identify manufacturing dates, lot numbers, expiration dates, and other information about the same product to enable better distribution control. The level of identification needed may vary depending upon the intended use.

Bar code symbologies are efficiently designed to support a specific industry need rather than a wide range of needs. A number of bar code symbologies are presently being used to track products throughout their life expectancy as they are manufactured, distributed, stored, sold, serviced, and disposed of. The bar code symbology designed for one application, however, may not suffice the needs of another application.

Bar codes have the advantage of being inexpensive, but require optical line-of-sight for reading and in some cases appropriate orientation of the bar code relative to the sensor. Additionally, they often detract from the appearance of the product label or packaging. Finally, damage to even a relatively minor portion of the bar code can prevent successful detection and interpretation of the bar code.

RFID tags have the advantage of supporting omnidirectional reading, but are comparatively expensive. Additionally, the presence of metal or liquid can seriously interfere with RFID tag performance, undermining the omnidirectional reading advantage. Passive (reader-powered) RFID tags are projected to be priced at 10 cents each in multi-million quantities by the end of 2003, and at 5 cents each soon thereafter, but this still falls short of the sub-one-cent industry target for low-price items such as grocery. The read-only nature of most optical tags has been cited as a disadvantage, since status changes cannot be written to a tag as an item progresses through the supply chain. However, this disadvantage is mitigated by the fact that a read-only tag can refer to information maintained dynamically on a network.

A two-dimension barcode is a new technology of information storage and transmission, which is widely used in various applications, including product identification, security and anti-counterfeiting, and E-commerce. The two-dimension barcode records information data with specific geometric patterns of black and white graphic symbols arranged in two-dimensional directions. The concept of logical basis of "0" and "1" bit stream adopted in computer systems is utilized to form graphic symbols that correspond to binary representation of text and numerical information. The graphic symbols can be read by an image input device or a photoelectric scanning device to achieve automatic information processing.

International standards of the two-dimension barcode include for example PDF417, Data Matrix, Maxi Code, and QR (Quick Response) Code, among which QR code is most widely used. The QR code shows an advantage of high-speed and all-direction (360 degrees) accessibility, and is capable of representation of Chinese characters, rendering QR code wide applicability in various fields. The QR code comprises a square array of a series of small square message blocks, in which "0" or "1" are represented through variation of gray levels of bright and dark blocks.

Chromatographic and Mass Spectrometric Analysis

GC is the most widely used technique in herbicide and cannabinoid chemical analysis, but it cannot be used directly to analyze all cannabinoids owing to limitations in volatility of the compounds. chemical analysis of *Cannabis* by GC has been reviewed [34]. Although the cannabinoids have very similar structural features, adequate separations of most of these compounds have been achieved on a number of commercially-available stationary phases. The most widely used are fused silica non-polar columns such as HP-1 and HP-5 as well as DB-1 and DB-5. Identification of the constituents is most readily performed by MS: un-derivatized 1, 3 and 6 show characteristic peaks at m/z values of 314, 246, 231, 193, 174 and 121, of 314, 299, 271, 231 and 55, and of 310, 296, 295 and 238, respectively [35].

Although GC chemical analysis is suitable for plant cannabinoids, the method is restricted to the determination of the quality of *Cannabis* for smoking if used directly since it can only provide information about the decarboxylated cannabinoids such as Δ9-THC [17]. Many GC reports concern non-derivatization methods because the target of most chemical analysis is the main neutral cannabinoids, and also because it is very difficult to obtain a complete derivatization of a sample for the purposes of quantification. The carboxyl group is not very stable and is easily lost as $CO_2$ under influence of heat or light, resulting in the corresponding neutral cannabinoids: THC, cannabidiol (CBD) and cannabigerol (CBG) [36]. These are formed during heating and drying of harvested plant material, or during storage and when *Cannabis* is smoked [37] [38] [39].

The variable conditions during all stages of growing, harvesting, processing, storage and use also induce the presence of breakdown products of cannabinoids. The most commonly found degradation product in aged *Cannabis* is cannabinol (CBN), produced by oxidative degradation of THC under the influence of heat and light [40]. In order to quantify the "total THC content" once present in the fresh plant material, the concentrations of degradation products have to be added to THCA and THC contents.

A number of compounds have been used successfully as internal standards for quantitative chemical analysis. In particular, 5α-cholestane (Matsunaga et al., 1990), docosane (Ferioli et al., 2000) and tetracosane (Stefanidou et al., 2000) are commonly employed because of their suitability for use with a flame ionization detection (FID). A recent development involves the use of deuterated cannabinoids as internal standards when MS detection is employed. Hexadeuterated (d6)-Δ9-THC gives a better linearity of measurement than (d3)-Δ9-THC (Joern, 1992) and can also be used as a standard in HPLC because it has a different retention time than 3. Ross et al. (2000) employed (d9)-Δ9-THC as a reference compound in order to demonstrate that no cannabinoids are present in *Cannabis* seeds even in the drug phenotype: the cannabinoids often found on the seed surface probably arise from contamination during harvesting.

Electrochemical Techniques

Previous work has shown that it is possible to detect the phenol part of complex molecules by reaction with an electrochemically-generated reagent [41]. In this protocol, the loss of dichloro-benzoquinone monoamine can be monitored electrochemically as it reacts with the substituted phenol of choice. Known as the Gibbs reagent (FIG. 2), it has been used to detect substituted phenols spectrophotometrically, where it has been observed that the most easily displaced substitutes (good anionic-leaving groups) give rise to high yields of dichloroindophenol, while methylphenol and longer alkyl group substitutions such as hydroxybiphenyl, ethylphenol and hydroxybenzoic acid gave no detectable colored product. It has been reported that phenol and phenoxyphenol give good yields of colored products (60 and 63%, respectively), methylphenol gives a low yield (18%), while nitrophenol produces a negative Gibbs reaction [42]. However, this technique is based on observing the product of the Gibbs (or related) reaction, not the consumption of the reagent.

A range of substituted phenols were investigated to determine the versatility of the indirect voltammetric method. This technique is based on the electrochemical oxidation of 2,6-dichloro-p-amino-phenol dissolved in aqueous solution which produces quinoneimine (QI) as shown in FIG. 3. On addition of Δ-THC the reduction wave, corresponding to the electrochemical reduction of quinoneimine (QI) back to aminophenol (AP), as shown in FIG. 3, reduces in magnitude since the QI chemically reacts with Δ-THC providing a useful analytical signal. This methodology is extremely attractive since it avoids the direct oxidation of Δ-THC which can lead to electrode passivation [43]. In similar work, graphite powder was modified with 4-amino-2,6-diphenylphenol which was abrasively immobilized onto a basal plane pyrolytic graphite electrode and assessed for the indirect electrochemical sensing of Δ-THC in saliva [44]. In this way, the detection technique based on the electrochemical formation of the QI was entirely surface confined in respect of the specific agent detecting the *Cannabis* related material.

Immunoassay Techniques

Immunoassays seem promising for studying cannabinoid metabolites because they are very sensitive, they are able to identify a small class of closely related compounds, and they can be applied directly to the sample without prior extraction or purification. The major problem with immunoassays is, however, one of selectivity. These methods need high-affinity, specific antibodies, but obtaining a very specific antibody that will only bind to one specific antigen is not an easy task since most antibodies bind to a group of closely related compounds. Thus, while immunoassays are particularly suited for screening purposes, positive immunoassay tests should be followed by further confirmative chemical analysis to exclude false positive results [45] [46]. Indeed, according to recent European Union recommendations on testing for drug abuse, and to the USA Mandatory Guidelines for Federal Workplace Drug Testing Programs, chromatographic techniques should always be used to confirm the results obtained by screening with immunoassays [46].

Four main immunoassay techniques are used in screening for cannabinoids, namely, radioimmunoassay (RIA), fluorescence polarization immunoassay (FPIA), enzyme multiplied immunoassay technique (EMIT), and enzyme-linked immunosorbent assay (ELISA). All of these methods are based on the competitive binding of a labeled antigen and unlabeled antigens from the sample with a limited, known amount of an antibody in the reaction mixture. The RIA and FPIA strategies are very similar in that both determine unbound antigen by either radioactive or fluorescent measurement. In RIA, the bound antigen should be separated from the unbound antigen before radioactivity measurement and, for this purpose, a second antibody is required. The principle of FPIA is that the fluorophore on the free antigen will emit light at a different plane compared with that on the bound antigen.

The measurement of the retention of polarization may be performed without physically separating the bound and the unbound antigens [47]. EMIT is based on the absorbance change produced by the reduction of NAD to NADH coupled to the oxidation of glucose-6-phosphate to 6-phosphogluconolactone, a reaction catalyzed by the enzyme glucose-6-phosphate dehydrogenase attached to the free antigen. The concentration of analyte in the sample determines the amount of free antigen that is labeled with the enzyme, and this is indirectly determining the change in absorbance that is measured [47]. Currently there is only one report of the chemical analysis of plant cannabinoids by immunoassay [48] in which Δ9-THC was measured in a methanolic leaf extract by FPIA using a highly selective monoclonal antibody. The result was confirmed by GC and the immunoassay showed good linear correlation (r=0.977) with the chromatographic method.

Drawbacks and Limitations of Previous Approaches

While tremendous advances have been made in many aspects of the process of sampling volatile components of many samples, the analytical process is still largely time-consuming and expensive, requiring sophisticated technology and highly trained individuals to perform the chemical analysis. There is a great need for simpler and less expensive processes to make such analyses available to a wider audience, who have less technical experience and smaller budgets available for analytical work. Examples of situations where such analytical work would really benefit the customer include groceries and food stores, where staff and customers could ascertain the "organic" quality of grains, produce and meats through a rapid chemical analysis of the content of pesticides, herbicide and other potential contaminants of the commodities that they are buying; the growers and distributers of such commodities, such that they could guarantee the "organic" quality of their products; microbreweries and home brewers, who wish to ascertain the quality of the grains, rice and other commodities used in brewing beer; tobacco farmers and distributors, who wish to determine the nicotine content of tobacco leaves and other products during harvest and distribution; medical marijuana growers, dispensaries, regulators and customers, who wish to ascertain the THC content of hemp and marijuana leaves and other products during harvest and distribution, so as to ascertain the value of their commodities and certify the potency of their products. Therefore, there is a great need for a new technology that separates the sampling process from the chemical analysis process, so as to make the overall chemical analysis more widely available to a larger, less technical market.

In the present disclosure, where a document, act or item of knowledge is referred to or discussed, this reference or discussion is not an admission that the document, act or item of knowledge or any combination thereof was at the priority date, publicly available, known to the public, part of common general knowledge or otherwise constitutes prior art under the applicable statutory provisions; or is known to be relevant to an attempt to solve any problem with which the present disclosure is concerned.

While certain aspects of conventional technologies have been discussed to facilitate the present disclosure, no technical aspects are disclaimed and it is contemplated that the claims may encompass one or more of the conventional technical aspects discussed herein.

REFERENCES

[1] B. Gilbert-Lopez, J. F. Garcia-Reyes and A. Molina-Diaz, "Sample treatment and determination of pesticide residues in fatty vegetable matrices: A review," TALANTA, vol. 79, no. 2, pp. 109-128, 2009.

[2] M. LeDoux, "Analytical methods applied to the determination of pesticide residues in foods of animal origin. A review of the past two decades," JOURNAL OF CHROMATOGRAPHY A, vol. 1281, no. 8, pp. 1021-036, 2011.

[3] K. Ridgway, S. P. D. Lalljie and R. M. Smith, "Sample preparation techniques for the determination of trace residues and contaminants in foods," JOURNAL OF CHROMATOGRAPHY A, vol. 1153, pp. 36-53, 2007.

[4] P. Zollner, A. Leitner, D. Berner, M. Kleinova, J. Jodlbauer, B. Mayer and W. Lindner, "Improving LC-MS/MS analyses in complex food matrices, Part I—Sample preparation and chromatography," LC GC EUROPE, vol. 16, no. 3, p. 163, 2003.

[5] C. Ferrer, M. Gomez, J. Garcia-Reyes, I. Ferrer, E. Thurman and A. Fernandez-Alba, "Determination of pesticide residues in olives and olive oil by matrix solid-phase dispersion followed by gas chromatography/mass spectrometry and liquid chromatography/tandem mass spectrometry," JOURNAL OF CHROMATOGRAPHY A, vol. 1069, no. 2, pp. 183-194, 2005.

[6] F. Calbiani, M. Careri, L. Elviri, A. Mangia, L. Pistara and I. Zagnoni, "Development and in-house validation of a liquid chromatography-electrospray-tandem mass spectrometry method for the simultaneous determination of Sudan I, Sudan II, Sudan III and Sudan IV in hot chili products," JOURNAL OF CHROMATOGRAPHY A, vol. 1042, pp. 123-130, 2004.

[7] J. Hajslova and J. Zrostlikova, "Matrix effects in (ultra) trace chemical analysis of pesticide residues in food and biotic matrices," JOURNAL OF CHROMATOGRAPHY A, vol. 1000, pp. 181-197, 2003.

[8] H. Aramaki, "Forensic chemical study on Marihuana 1. A detection method of the principal constituents by thin-layer and gas chromatography," Chemical and Pharmacological Bulletin, vol. 16, no. 5, pp. 822-826, 1968.

[9] K. D. Parker, "Rapport préliminaire sur la separation et la determination quantitative par la chromatographic sur couches minces et la chromatographic en phase gazeuse des constituents cannabiniques présents dans la plante ou ajoutés A l'urine," Bulletin des stupéfiants, vol. 20, no. 4, pp. 7-12, 1968.

[10] R. A. de Zeeuw, T. M. Malingre and F. Merkus, "Δ-1-Tetrahydro-cannabinolic acid, an important component in the evaluation of Cannabis products," Journal of Pharmacy and Pharmacology, vol. 24, no. 1, pp. 1-6, 1972.

[11] M. R. Paris and R. R. Paris, "Importance de la chromatographic pour l'étude des constituents du Cannabis sativa L," Bulletin de la Société chimique de France, vol. 1, pp. 118-122, 1973.

[12] C. E. Hadley and K. Turner, "Constituents of Cannabis sativa L. 11: Absence of cannabidiol in an African variant," Journal of Pharmaceutical Sciences, vol. 62, no. 2, pp. 251-255, 1973.

[13] S. N. Sharma and J. D. Tewari, "Separation and identification of cannabinoids from Cannabis indica L. by thin-layer chromatography," Pharmazie, vol. 34, no. 1, pp. 54-55, 1979.

[14] P. Oroszlan, "Separation, quantitation and isolation of cannabinoids from Cannabis sativa by overpressure layer chromatography," Journal of Chromatography, vol. 388, no. 1, pp. 217-224, 1987.

[15] P. B. Baker, "Determination of the distribution of cannabinoids in Cannabis resin using high-performance liquid chromatography," Journal of Analytical Toxicology, vol. 4, pp. 145-152, 1980.

[16] C. G. Vaughan and R. N. Smith, "High-pressure liquid chromatography of Cannabis: quantitative chemical analysis of acidic and neutral cannabinoids," Journal of Chromatography, vol. 129, pp. 347-354, 1976.

[17] S. L. Kanter, M. R. Musumeci and L. E. Hollister, "Quantitative determination of Δ-9-tetrahydrocannabinol and Δ-/9-tetrahydro-cannabinolic acid in marihuana by high-pressure liquid chromatography," Journal of Chromatography, vol. 171, pp. 504-508, 1979.

[18] D. J. Harvey, "Chemistry, metabolism and pharmacokinetics of the cannabinoids," in Marihuana in Science and Medicine, New York, Raven Press, 1984, pp. 37-107.

[19] D. Debruyne, "Identification et différenciation des chanvres résineux et textile: utilisation conjuguée de HPLC et GLC haute resolution," Bulletin des stupéfiants, vol. 33, no. 2, pp. 45-54, 1981.

[20] I. Centini et al., "Packed-column chromatography, high-resolution gas chromatography and high-pressure liquid chromatography in comparison for the chemical analysis of Cannabis constituent," Forensic Science International, vol. 21, no. 2, pp. 129-137, 1983.

[21] I. Nakahara, "Studies on confirmation of Cannabis use. I. Determination of the cannabinoid contents in marijuana cigarette, tar, and ash using high-performance liquid chromatography with electrochemical detection," Journal of Analytical Toxicology, vol. 9, no. 3, pp. 121-124, 1985.

[22] T. B. Vree, "Gas chromatography of *Cannabis* constituents and their synthetic derivatives," Journal of Chromatography, vol. 74, pp. 209-224, 1972.

[23] M. Novotny et al., "Chemical analysis of marijuana samples from different origins by high resolution gas-liquid chromatography for forensic application," Analytical Chemistry, vol. 48, no. 1, pp. 24-29, 1976.

[24] L. Stromberg, "Minor components of *Cannabis* resin. VI. Mass spectrometric data and gas chromatographic retention times of components eluted after cannabinol," Journal of Chromatography, vol. 121, pp. 313-322, 1976.

[25] D. J. Harvey, "Comparison of fourteen substituted silyl derivatives for the characterization of alcohols, steroids and cannabinoids by combined gas-liquid chromatography and mass spectrometry," Journal of Chromatography, vol. 147, pp. 291-298, 1978.

[26] H. Spiteller and G. Grote, "Neue cannabinoide. II," Journal of Chromatography, vol. 154, pp. 13-23, 1978.

[27] E. Commission, Community method for the quantitative determination of Δ9-THC (Tetrahydrocannabinol) content in hemp varieties, Off J Eur Comm L280:43-65: Commission Regulation (EC) No 2316/1999 laying down detailed rules for the application of Council Regulation (EC) No 1251/1999 establishing a support system for producers of certain arable crops, 1999.

[28] C. Arthur and J. Pawliszyn, Anal Chem, vol. 62, pp. 2145-2148, 1990.

[29] H. Kataoka, H. Lord and J. Pawliszyn, Journal of Chromatography A, vol. 880, p. 35-62, 2000.

[30] R. Smith, "High-pressure liquid chromatography of *Cannabis* identification of separated constituents," J. Chromatogr., vol. 115, pp. 101-106, 1975.

[31] S. Kanter, M. Musumeci and L. Hollister, "Quantitative determination of D9-tetrahydrocannabinol and D9-tetrahydrocannabinolic acid in marihuana by high pressure liquid chromatography," J Chromatogr, vol. 171, p. 504-508, 1979.

[32] J. Turner and P. Mahlberg, "Effects of sample treatment on chromatographic chemical analysis of cannabinoids in *Cannabis sativa* L. (Cannabaceae)," J. Chromatogr., vol. 283, p. 165-171, 1984.

[33] T. Veress, J. Szanto and L. Leisztner, "Determination of cannabinoid acids by high-performance liquid chromatography of their neutral derivatives formed by thermal decarboxylation process in an open reactor," J. Chromatogr., vol. 520, pp. 339-347, 1990.

[34] J. Parker and B. Stembal, "Review of gas-liquid chromatography of marihuana," JAOAC, vol. 57, p. 888-892, 1974.

[35] S. Chang, C. Chen, F. Chin and H. Chang, "Qualitative and quantitative chemical analysis of cannabinoids in *Cannabis sativa*, Huo-Ma-Jen and Agave Sisalan," Chin Pharm J, vol. 49, pp. 77-80, 1997.

[36] G. Thakur, R. Duclos Jr. and A. Makriyannis, Life Sci, vol. 78, p. 454, 2005.

[37] C. Giroud, Chimia, vol. 56, p. 80, 2002.

[38] K. Hillig and P. Mahlberg, Am. J. Bot., vol. 91, p. 966, 2004.

[39] N. Doorenbos, P. Fetterman, M. Quimby and C. Turner, Ann. N. Y. Acad. Sci., vol. 191, p. 3, 1971.

[40] A. Stolker, J. van Schoonhoven, A. de Vries, I. Bobeldijk-Pastorova, W. Vaes and R. van den Berg, J. Chromatogr. A, vol. 1058, p. 143, 2004.

[41] E. R. Lowe, R. G. Compton and C. E. Banks, "Indirect detection of substituted phenols and *Cannabis* based on the electrochemical adaptation of the Gibbs reaction," Anal Bioanal Chem, vol. 383, p. 523-531, 2005.

[42] P. Josephy and A. Damme, Anal Chem, vol. 56, p. 813, 1984.

[43] N. Craft, G. Byrd and L. Hilpert, Anal Chem, vol. 61, p. 540, 1989.

[44] A. Goodwin, C. E. Banks and R. G. Compton, "Graphite Micropowder Modified with 4-Amino-2,6-diphenylphenol Supported on Basal Plane Pyrolytic Graphite Electrodes: MicroSensing Platforms for the Indirect Electrochemical Detection of D9-Tetrahydrocannabinol in *Saliva*," Electroanalysis, vol. 18, no. 11, pp. 1063-7, 2006.

[45] C. Moore, A. Negrusz and D. Lewis, "Determination of drugs of abuse in meconium," J Chromatogr B, vol. 713, p. 137-146, 1998.

[46] I. Breindah and K. Andreasen, "Determination of 11-nor-Δ-tetrahydro-cannabinol-9-carboxylic acid in urine using HPLC and electrospray ionisation mass spectrometry," J Chromatogr B, vol. 732, pp. 155-164, 1999.

[47] M. Weaver, B. Gan, E. Allen, L. Baugh, F. Liao, R. Liu, J. Langner, A. Walia and L. Cook, "Correlations on radioimmunoassay, fluorescence polarization immunoassay and enzyme immunoassay of *Cannabis* metabolites with gas chromatography/mass spectrometry chemical analysis of 11-nor-D9-tetrahydrocannabinol-9-carboxylic acid in urine specimens," Forensic Sci Int, vol. 49, p. 43-56, 1991.

[48] M. Bacigalupo, A. lus, G. Meroni, G. Grassi and A. Moschella, "Time-resolved fluoro-immunoassay for D9-tetrahydrocannabinol as applied to early discrimination of *Cannabis sativa* plants," J Agric Food Chem, vol. 47, p. 2743-45, 1999.

[49] Ngen-Ngwainbi, et al., J. Am. Chem. Soc., vol. 108, pp. 5444-5447, 1986.

[50] B. S. Yu et al., "Electrochemical oxidation of phenol on metal oxide electrodes," JOURNAL OF WATER CHEMISTRY AND TECHNOLOG, vol. 34, no. 1, pp. 24-27, 2012.

[51] D. W. Lachenmeier, L. Kroener, F. Musshoff and B. Madea, "Determination of cannabinoids in hemp food products by use of headspace solid-phase microextraction and gas chromatography-mass spectrometry," Anal Bioanal Chem, vol. 378, p. 183-189, 2004.

[52] D. W. Lachenmeier, L. Kroener, F. Musshoff and B. Madea, "Determination of cannabinoids in hemp food products by use of headspace solid-phase microextraction and gas chromatography-mass spectrometry," Anal Bioanal Chem, vol. 378, p. 183-189, 2004.

BRIEF SUMMARY

The present disclosure relates to a distributable sampling and sensing instrument for chemical analysis of consumable foods and other agricultural products. The distributed sampling system is used to separate and concentrate the chemicals of interest obtained from samples at remote locations via thermal desorption onto a detachable target substrate that can be analyzed on-site or off-site. The volatile components adsorbed onto the target substrate can be analyzed with specific sensors (e.g., electrochemical sensors) or the assembly can be sent to a central lab and analyzed with conventional chemical instrumentation (e.g., GC-MS). This instrument provides the capability to enable chemical analysis of a wide range of chemical species of interest in a wide range of environments and conditions.

The present disclosure provides a device, system, and associated methods that will actively or passively sample a material (solid, liquid or gas) by heating the sample, volatilizing it into the gas phase and directing it onto the surface of a substrate. The substrate is composed of a material (either a solid, or a liquid-coated solid) that has both high surface area and an active surface with excellent adsorptive properties. These properties can be tailored for retention of specific components or provide for broad adsorption of materials with general chemical properties. Accordingly, the disclosure provides methods for sampling and chemical analysis of samples to determine the chemical compounds thereof at low concentrations. The disclosure also describes instrumentation for the chemical analysis of materials adsorbed onto this substrate, whether that chemical analysis is directly coupled to the sampling step, or removed in distance and in time from the sampling event.

The present disclosure addresses at least one of the foregoing disadvantages. However, it is contemplated that the present disclosure may prove useful in addressing other problems and deficiencies in a number of technical areas. Therefore, the claims should not necessarily be construed as limited to addressing any of the particular problems or deficiencies discussed hereinabove. To the accomplishment of the above, this disclosure may be embodied in the form illustrated in the accompanying drawings. Attention is called to the fact, however, that the drawings are illustrative only. Variations are contemplated as being part of the disclosure.

BRIEF DESCRIPTION OF THE DRAWINGS

In the drawings, like elements are depicted by like reference numerals. The drawings are briefly described as follows.

Figure 1:
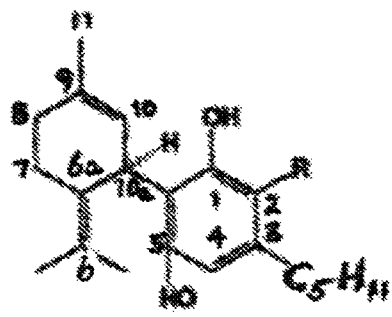
FIG. 1 is a plurality of chemical structural formulas of common cannabinoid molecules.
Figure 1:
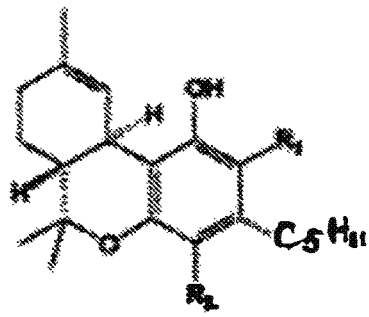
Figure 1:
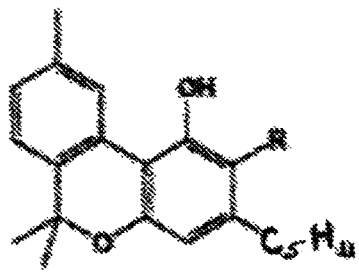
Figure 1:
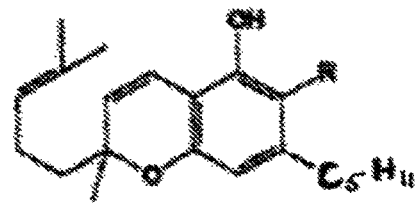
Figure 2:
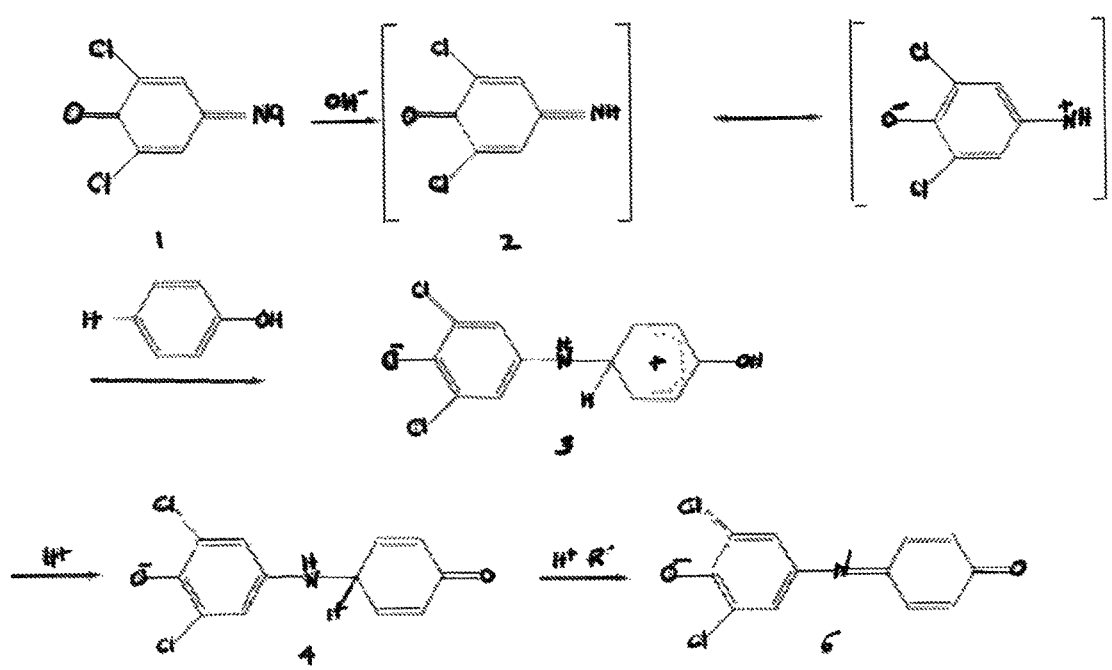
FIG. 2 is a representation of a reaction mechanism aminophenols in the Gibbs reaction.

The present disclosure now will be described more fully hereinafter with reference to the accompanying drawings, which show various example embodiments. However, the present disclosure may be embodied in many different forms and should not be construed as limited to the example embodiments set forth herein. Rather, these example embodiments are provided so that the present disclosure is thorough, complete and fully conveys the scope of the present disclosure to those skilled in the art.

DETAILED DESCRIPTION OF THE PREFERRED EMBODIMENTS

It is to be understood that both the foregoing general description and the following description are exemplary and explanatory only and are not restrictive of the methods and devices described herein. In this application, the use of the singular includes the plural unless specifically state otherwise. Also, the use of "or" means "and/or" unless state otherwise. Similarly, "comprise," "comprises," "comprising," "include," "includes," "including," "has," "have," and "having" are not intended to be limiting.

Headings are provided to organize the disclosure to provide ease with reading and are not intended to be limitations or have any legal standing.

Broadly stated, embodiments of the present disclosure provide analytical methods, instruments, and devices that address the shortcomings addressed above. The present disclosure provides a device, system, and associated methods that will actively or passively sample a material (solid, liquid or gas) by heating the sample, volatilizing it into the gas phase and directing it onto the surface of a substrate. The substrate is composed of a material (either a solid, or a liquid-coated solid) that has both high surface area and an active surface with excellent adsorptive properties. These properties can be tailored for retention of specific components or provide for broad adsorption of materials with general chemical properties. Accordingly, the disclosure provides methods for sampling and chemical analysis of samples to determine the chemical compounds thereof at low concentrations. The disclosure also describes instrumentation for the chemical analysis of materials adsorbed onto this substrate, whether that chemical analysis is directly coupled to the sampling step, or removed in distance and in time from the sampling event. A sample tracking interface is provided using a method for reading sample identification information present in a first region of the encoded physical medium and then correlating the measured information with the sample identification information has been encoded therein. According to one embodiment, the information may be encoded according to a spatial encoding scheme, a bar code scheme, or a combination thereof.

In one embodiment, the disclosure provides a method for detecting an analyte contained in a solid comprising the steps of heating the solid, directing a gas evolved from such heated solid comprising single or multiple chemical analyte(s) onto the surface of an adsorptive substrate (particularly a "target substrate," as defined herein) in a sealed gas fluidic system for a period of time sufficient for the analyte to be adsorbed onto the surface; and then analyzing the analyte. The analyte can be analyzed directly, for example, by contacting said target substrate with a sensor, and quantitatively and/or qualitatively evaluating the chemical composition of the analyte(s) on said substrate by the response of the sensor.

In another embodiment, the target substrate thus obtained can be removed from the sampling instrument and placed in a suitable container that preserves the composition of the analyte within the target substrate, then shipped to a laboratory that contains appropriate instrumentation for chemical analysis. Once there, the analyte(s) contained within the target substrate can be analyzed with conventional analytical instrumentation commonly used for chemical separations (including gas chromatography (GC), high performance liquid chromatography (HPLC), thin layer chromatography (TLC) or any of a variety of other methods used for chemical separations) and these methods can be coupled with appropriate detection methods (such as flame ionization detection, mass spectrometry, UV or visible light absorbance, infrared or neat infrared absorbance spectroscopy, or other related methods). Such chemical analysis can be done directly (for example, by placing the target substrate in the appropriate analytical instrument and performing the chemical analysis) or after extraction, where the target substrate is placed in a minimum volume of an appropriate solvent, and the analyte(s) are solubilized in the solvent. The resulting solution can then be used as the sample matrix for chemical analysis (for example, the solution can be injected into a GC-MS or an HPLC-UV absorbance detector).

In one aspect of the present disclosure, an apparatus for creating volatile components of a substance is disclosed. The apparatus comprises in combination a power source, a heater, a pump sufficient to create a gas flow, a temperature sensor, time and temperature control, a source material holder for holding the sample substance which is connected via inert tubing to a second receptacle for holding a target substrate that receives the vapor that results from the release of volatile components created by heating the sample and releasing volatile elements in a sealed gas fluidic system. The pump may create positive pressure at the sample source sufficient to push the evolved gas through the target substrate, or it may be a vacuum pump that creates a negative pressure at the target substrate, such that the evolved gas is "sucked" from the sample chamber thru the target substrate without releasing the gas to ambient atmosphere. The temperature sensor may be a thermocouple or resistance temperature detector (RTD) or other device suitable for monitoring temperature. The heater may be a Ceramic UF Heater, simply resistive heating tape wrapped around the sample container, or other suitable heating device. The airflow may be between 0.1 and 100 mL/min. The apparatus is not meant to release volatile elements into the ambient air without prior removal of volatile components generated during heating. Also, the time and temperature controllers may produce a variable heat according to the specific substance being volatized in said apparatus.

The apparatus may further comprise an information input/output device in communication with the power supply that displays the relevant parameters and allows for adjustment of said parameters by controlling relevant components within the apparatus. It should be understood that the information input/output device may be in communication in a multitude of ways including wireless and fiber optic communication. Information may be manually inputted or programmed to be controlled automatically by the equipment into the information input/output device which in turn electrically communicates with the power, heater and pumps to adjust the temperature, flow rate and duration of the sampling process within said apparatus for a specified time. The time elapsed, temperature, and other desired information may be displayed on a display such as an LCD display. Also, an information retrieval and delivery means in electrical, optical or wireless communication with said device may be used. This may be a USB, firewire, Ethernet, wireless Ethernet, ilink interface, NV interface, telephone cable interface, parallel interface, fiber optics, serial interface or other communication method connected to the apparatus and an information source (e.g. computer). The information retrieval and delivery means may be a disk contained within the apparatus, or it may be transmitted via the aforementioned communication protocols to an external information source. The temperature provided by the heater means is preferably between 0° C. and 300° C.

The present disclosure improves the sample tracking interface by providing a method for interfacing via an encoded physical medium having a region wherein information has been encoded. The interface method includes reading sample identification information present in a first region of the encoded physical medium and then correlating the measured information with the sample identification information has been encoded therein. According to one embodiment, the information may be encoded according to a spatial encoding scheme, a bar code scheme, or a combination thereof. The present disclosure also teaches that when it is determined that the marker is present in the first region, the certain encoded information is translated into certain decoded information including a function to be performed by the computer system. The function to be performed by the computer system may include, among other things, providing a link to a webpage containing sample chemical analysis information. The certain decoded information could also include a uniform resource locator (URL) and the function may involve the computer system accessing and/or displaying an Internet web page to which the URL directs.

The present disclosure further improves upon the sample tracking interface by teaching a method for generating an encoded physical medium having a region with encoded content. The method requires receiving content that is to be encoded into a desired location on the encoded physical medium, encoding the content according to a particular encoding scheme suitable for application onto the encoded physical medium, and inserting the encoded content together with a marker into a corresponding desired location within a representation of the encoded physical medium. The marker indicates that the content is encoded within the corresponding desired location, thereby enabling a subsequently engaged sensor to determine the existence of the content. Once the representation is created, the present disclosure further teaches that the encoded physical medium may be generated from the representation.

The present disclosure further teaches maintaining a database tracking the results of the user engaging the sensor with a plurality of samples, including the determination of multiple chemical components within a given sample. The database could then be used later to determine whether a specific condition (i.e., cannabinoid content exists within a given range) has been satisfied. In turn, a specified action could be specified by the computer system (i.e., satisfy quality control release criteria).

One separate embodiment of the present disclosure teaches a computer interface between the sample, a user and a computer system using an encoded physical medium. The encoded physical medium is suitable for having at least one region wherein information has been encoded. The computer interface includes a sensor operable for measuring information present on the encoded physical medium, and a first device coupled to the sensor and responsive to determine whether information measured by the sensor includes a marker indicating that certain encoded information is present in the measured information. In a related embodiment, the computer interface includes a second device responsive to the first device such that when the first device determines the presence of the specified content, the second device is operable to decode the certain encoded information present in the measured information. In yet another related embodiment, the computer interface also has a transmitter device operable to transmit the certain decoded information to the computer system.

According to another embodiment, an apparatus for releasing volatile elements of a substance in a sealed gas fluidic system is disclosed comprising in combination a power source in electrical communication with a heater and a pump, a thermocouple for sensing temperature, an information retrieval and delivery means in electrical communication with the power source, a time and temperature control device that adjusts the heat produced by the heater means and length of time heat is produced, information output means in electrical communication with the power means that displays the temperature and time, a source material holder for holding the substance connected via inert tubing to a target substrate holder for holding the target substrate. The time and temperature control means produces a variable heat according to the specific substance being volatized in a sealed gas fluidic system in the apparatus. The heat provided by the heater means is preferably between 0° C. and 300° C. and the gas flow between 0.1 and 100 mL/min. The heater can be energized at a defined rate, so as to create a programmed thermal cycle. This programmed thermal cycle allows the gradual heating of the sample, so that analytes with lower boiling points are volatilized first and removed from the sample before the heater produces temperatures that could decompose those materials. The heating is continued to volatilize additional higher boiling components and all those analytes are swept to the target substrate in a sealed gas fluidic system and adsorbed. In this way, a range of analytes of different boiling points can be effectively transferred to the target substrate without inducing thermal decomposition of the lower boiling materials.

The composition of the target substrate can be varied to alter the selectivity of the adsorption process. The selectivity of adsorption is determined by the chemical composition of the target substrate material, and as a general rule, the doctrine, "like dissolves like," is applied. For example, if the target analyte is composed of hydrophobic material, then a hydrophobic target material is selected, since it is likely to adsorb the analyte more strongly. Similarly, if the analyte is hydrophilic, then a hydrophilic target material is selected. If the sample contains a variety of different chemicals with different solubilities, then the target substrate can comprise a combination of materials to adsorb the analytes.

Alternatively, the chemical composition of the target substrate can be altered by adding a thin film, or stationary phase to the surface of the substrate. As conventionally used in many chromatographic techniques, the stationary phase can consist of almost any material that can be deposited as a thin film and that forms a stable layer. Examples of non-polar stationary phases include HP-1, HP-5 as well as DB-1 and DB-5, while other examples of stationary phases include hydrophilic or hygroscopic materials, e.g. based on cellulose, modified cellulose such as cellulose nitrate or cellulose acetate, hydroxyalkylated cellulose, or modified and unmodified cellulose crosslinked with substances such as epichlorhydrin. Also suitable are glass fiber matrices and matrices consisting of polyester. These materials can either be used solely or in combination with other compound materials with a hydrophilic portion in the carrier matrix prevailing.

In a preferred manner, the target substrate materials are structured so as to form particles (e.g. pearl-like, see DD-A296 005) or fibers, such as filter papers on cellulose basis (EP-A 374684, EP-A 0470565). Other materials used for the construction of the target substrate are described in EP-A 0 374 684, EP-A 0 353 570 and EP-A 353 501. The first carrier matrix must be gas-permeable to allow suitable animals with the corresponding immunogen. The enrichment of the immunologically active substance from the gas phase. For pressure gradients above the adsorber (200-500 mbar) which are technically easy to implement, the gas permeabilities advantageously range between 1 mL/min and 100 L/min, preferably between 10 mL/min and 100 mL/min.

In another embodiment, the target substrate's chemical composition can be altered through reaction with specific binding components. Biosensors making use of the principle of an immunological reaction between the analyte and binding partners contained in the biosensor would be potentially suitable for such tasks due to the high selectivity and specificity of the immunological reactions. A biosensor of this kind has been described by Ngen-Ngwainbi [49]. In this reference, an antibody to a cocaine metabolite (benzoylecgonine) as a reactive component of the sensor is used as a Piezo transducer with a resonance frequency of 9 MHz. The antibody is immobilized through physical adsorption on the surface of the sensor. The lower detection limit is at 0.5 ppb corresponding to $2\times10^{-11}$ mol/L in gas phase (for cocaine and cocaine-HCl).

The disclosure also includes devices and instruments for use in the methods of the disclosure. For example, the disclosure includes a device for active sampling of a gas and directing the same gas onto a target substrate comprising a gas conduit having a sample port and a sealed gas fluidic system; the sample port is fluidly connected to a target holder containing a target substrate, wherein the sample port is capable of directing a gas from the sample chamber onto a target substrate; and a pump for introducing the gas through the sample port and moving the gas through the target holder such that the analyte can adsorb onto the target substrate in a sealed gas fluidic system.

In another embodiment, the chemical composition of the analyte adsorbed onto the test substrate is determined by placing the test substrate in contact with an electrochemical sensor capable of sensing the desired analyte. The electrochemical sensor can monitor the presence of the phenolic molecule by direct oxidation of the phenol, for example, as shown for the electrochemical oxidation of phenol on a metal oxide electrode [50]. Alternatively, the electrochemical sensor can consist of a carbon electrode modified with reagents that emulate the Gibbs reaction. The present disclosure modifies or builds on the known Gibbs reaction by electrochemically oxidizing a p-aminophenol (PAP) to form a benzoquinone monoamine (for example, a dichloro- or diphenyl-benzoquinone monoamine), which then reacts with the substituted phenol compound of interest, as in the classical Gibbs reaction. Monitoring the reduction of an oxidized PAP provides an indirect method of detecting phenols and phenolic compounds, or example phenol, 4-phenoxyphenol, methylphenol (para and meta), nitrophenol, cannabinoids (e.g. tetrahydrocannabinol) and catechins (e.g. EGCG or ECG). The methodology according to the present disclosure is attractive since it avoids the direct oxidation of the phenol, which can lead to electrode passivation. The PAP may be present in the electrolyte and/or on the surface or in the bulk of the working electrode material.

In one embodiment of the disclosure there is provided an electrochemical sensor for the detection of a phenol-containing molecule, which comprises a first compound, a working electrode and an electrolyte in contact with the working electrode, wherein the first compound operatively undergoes a redox reaction at the working electrode to form a second compound which operatively reacts in situ with the phenol, wherein said redox reaction has a detectable redox couple and wherein the sensor is adapted to determine the electrochemical response of the working electrode to the consumption of said second compound on reaction with the phenol.

In another embodiment of the disclosure there is provided a method of sensing a phenol-containing molecule in a sample, comprising: (a) oxidizing a first compound at the working electrode of an electrochemical sensor to form a second compound which is operatively reactive with the phenol-containing molecule; (b) contacting the phenol-containing molecule with the second compound in the presence of an electrolyte, such that the second compound reacts with the phenol-containing molecule; and (c) determining the electrochemical response of the working electrode to the consumption of the second compound on reaction with the phenol-containing molecule.

In the present disclosure, phenol-containing molecules can be detected indirectly. A number of electrochemical biosensors have been developed for the monitoring of phenols in aqueous systems. Laccase, catechol oxidase, and tyrosinase have been used as biosensitive part of sensors in combination with other modifiers like carbon nanotubes (CNT), magnetic core-shell ($Fe_3O_4$—$SiO_2$) nanoparticles, and polypyrrole. This approach leads to improvement of determination analytical selectivity and sensitivity [50].

In particular, the present disclosure involves the use of a compound which operatively undergoes a redox reaction at the working electrode, wherein the reaction has a detectable redox couple and wherein the product of said reaction operatively reacts in situ with the phenol-containing molecule. The electro-chemical response of the working electrode to the consumption of the said compound on reaction with the phenol-containing molecule is then determined. The phenol-containing molecule may be contacted with the compound prior to, contemporaneously with or subsequent to the oxidation of the compound, but is typically admitted subsequent thereto.

In another embodiment of the disclosure, the choice of suitable sensor arrangement and materials is important when considering the moiety to be sensed, temperature range and electrochemical method to be used. Amperometric sensors have been found to enable low cost of components, small size, and lower power consumption than other types of sensor, and are ideal for use in portable chemical analysis systems. In the present disclosure, amperometric sensing methodology is typically employed.

The working electrode may be a screen-printed electrode, a metallic electrode, a metal nitride, a semiconductor, an edge plane pyrolytic graphite electrode, a basal plane pyrolytic graphite electrode, a gold electrode, a glassy carbon electrode, a boron doped diamond electrode, or a highly ordered pyrolytic graphite electrode. The working electrode may be a microelectrode or a macroelectrode.

Determination of the electrochemical response of the working electrode may comprise measuring the current flow between the working electrode and a counter electrode to determine the amount of phenol or phenolic compound. It is particularly preferred that the working electrode is operatively maintained at a constant voltage. In one embodiment, the current is measured using linear sweep or cyclic voltammetry. In another embodiment, said current is measured using square wave voltammetry. In an alternative embodiment, the current is measured using a pulsed voltammetry technique, in particular differential pulse voltammetry.

The following non-limiting Examples illustrate the disclosure.

Example 1

Sampling Procedures to determined cannabinoids in hemp products for by means of GC-MS. Sample preparation, extraction and gas chromatographic separation conditions were derived from a literature reference [51]. These are summarized below:

Reagents and Materials

Cannabidiol (CBD), cannabinol (CBN), Δ9-tetrahydrocannabinol (THC), and Δ9-tetrahydrocannabinol-d3 (THC-d3) were purchased from Promochem (Wesel, Germany). N-methyl-N-trimethylsilyltrifluoroacetamide (MSTFA) was obtained from Macherey-Nagel (Düren, Germany). A SPME device for an autosampler with a replaceable 100-μm polydimethylsiloxane (PDMS) fiber was obtained from Supelco (Deisenhofen, Germany). The SPME fiber was conditioned at 250° C. for one hour in the injection port of the gas chromatograph, according to the supplier's instructions. chemicals were purchased from Merck (Darmstadt, Germany).

GC-MS Method

GC-MS analyses were carried out on a HP 6890 Series Plus gas chromatograph coupled to a 5973N mass-selective detector (Agilent) and an autosampler. Data acquisition and chemical analysis were performed using standard software supplied by the manufacturer (Agilent Chemstation). Substances were separated on a fused silica capillary column (HP-5MS, 30 m×0.25 mm i.d., film thickness 0.25 μm). Temperature program: 160° C. hold for 1 min, 15° $min^{-1}$ to 190° C., hold for 1 min, 5° $min^{-1}$ to 250° C., hold for 1 min, 20° $min^{-1}$ to 300° C., hold for 2 min. The injection port, ion source, quadrupole, and interface temperatures were 250° C., 230° C., 150° C. and 280° C., respectively. Splitless injection mode was used and helium, with a flow rate of 1.0 mL $min^{-1}$, was used as carrier gas.

Samples and Sample Preparation

A diverse range of commercially available hemp food products were purchased from esoteric and nature stores and via the internet. All solid samples were blended and homogenized in a standard mixer. Liquid samples were homogenized by shaking. Hemp tea infusions were prepared by pouring 100 mL boiling water on 1.5 g tea. After 15 min, the infusion was filtered.

SPME Extraction

For HS-SPME extraction, approximately 50 mg (tea), 400 mg (chocolate, snack bar, thin slices), 100 mg (seed, flour, fruit bar, nibbles), 1000 mg (pastilles), 100 μL (oil), 500 μL (lemonade, beer), or 1000 μL (tea infusion, shampoo) sample were placed directly in a 10-mL headspace vial in the presence of 1 mL NaOH (1 mol $L^{-1}$), 0.5 g of sodium carbonate, and 100 μL aqueous internal standard solution (200 ng $mL^{-1}$ THC-d3). For on-coating derivatization, a separate vial containing 25 μL derivatization reagents (MSTFA for silylation) was prepared for each sample. The vials were sealed using a silicone/PTFA septum and a magnetic cap. The sample vial was shaken for 5 min at 90° C. in the agitator of the autosampler (650 rpm, agitator on time 0:05 min, agitator off time 0:02 min). For absorption, the needle of the SPME device containing the extraction fiber was inserted through the septum of the vial and the fiber was exposed to the headspace in the vial for 25 min. Then for derivatization the fiber was exposed for 8 min at 90° C. in a second vial containing 25 μL MSTFA. Finally, the SPME fiber with the absorbed and derivatized compounds was introduced into the injection port of the GC-MS for 5 min to accomplish complete desorption of the analytes.

Liquid-Liquid Extraction

For liquid-liquid extraction, 100 μL of the internal standard solution and 5 mL 9:1 (v/v) n-hexane-ethyl acetate were added to the same amount of sample; the mixture was homogenized for 15 min under ultrasonication and centrifuged for 5 min. The organic layer was separated and the lower layer was extracted another two times with 5 mL n-hexane-ethyl acetate. Alternatively, the oil samples were extracted three times with methanol. The combined organic extract was evaporated under nitrogen. The dried samples were derivatized with a mixture of 50 μL MSTFA, 20 pyridine, and 130 μL isooctane under incubation at 90° C. for 15 min. After transfer to GC injection vials 1 μL was injected for GC-MS chemical analysis.

Validation Studies

To examine the effect of the matrix on the SPME extraction process, multiple portions from 25 to 200 mg of hemp tea, hemp chocolate, and hemp oil were analyzed. For validation of the method, spiked samples were prepared, using olive oil, milk chocolate, and green tea as blank matrices. Precision and accuracy was determined by repeated chemical analysis of the spiked samples. The linearity of the calibration plots was evaluated between 0.1 and 4 mg kg$^{-1}$ (related to 100 mg weighed portion). For determination of the limits of detection (LOD) and quantitation (LOQ), separate calibration curves in the range of the LOD (0.005-0.5 mg kg$^{-1}$) were established.

Comparison of HS-SPME with Conventional LLE

For purposes of comparison all samples were analyzed using HS-SPME and LLE, and comparison of representative chromatograms from GC-MS chemical analysis of identical hemp tea samples using LLE and HS-SPME reveals the superiority of HS-SPME. In the LLE chromatogram several large matrix peaks elute in the retention-time range of the analytes, whereas when HS-SPME was used distinct peaks were acquired for all compounds with slight or little matrix interference.

This is in good agreement between levels of cannabinoids determined in food samples by HS-SPME and LLE [52]. The linearity of the correlation between HS-SPME and LLE was significant, with correlation coefficients of 0.992 (THC), 0.974 (CBD), and 0.985 (CBN). The slope and intercept of the regression lines show there is no constant or proportional difference between the two procedures. The limits of detection achieved by HS-SPME were comparable with those of already published methods applying conventional techniques; some were even better [52].

GC Results

Lachenmeier et. al. reported that when thirty authentic samples were analyzed by means of HSSPME with GC-MS, no matrix interferences were observed. Headspace extraction in combination with SPME separates the semi-volatile cannabinoids from non-volatile compounds. Peak purity and selectivity are ensured. Interfering peaks, often observed in GC-MS analyses for THC after conventional extraction and silylation, are excluded, because of lower matrix contamination [52].

Recoveries of the analytes, as determined by both HS-SPME and LLE, depend on their distribution coefficients in the equilibrium of the extraction process for both procedures [52]. LLE involves homogenization of the two liquid phases to accelerate adjustment of the equilibrium concentrations. However, it is not possible to homogenize the phases in HS-SPME (since it is a two-phase system), therefore the transfer of the molecules from the liquid to the gas phase is rate determining. Matrix properties such as viscosity or lipophilicity therefore affect the headspace procedure to a large extent, so the speed of diffusion of the analytes in the matrix is crucial. Extraction recoveries for simpler matrices (e.g. tea) were found to be proportional to the amount of sample.

Complex lipid- and protein-containing matrices, for example chocolate, caused significant matrix retention and lower recoveries [52]. Suppression of HS-SPME extraction recovery by lipid material has previously been reported, and the only way this could be mitigated was through the use of alkaline hydrolysis to saponify the lipids. They found that this resulted in low extraction yields, but it was possible to determine the cannabinoids reproducibly and automatically by using a versatile and programmable autosampler. Although the matrix varies considerably for the foods studied, the sensitivity of the procedure was sufficient to determine whether the THC content of the foods was within the guidance values.

Example 2

Electrochemical Materials and Methods. Sample preparation, extraction and gas chromatographic separation conditions were derived from a literature reference [41]. These are summarized below:

Chemical and Materials:

All chemicals were of analytical grade and used as received without any further purification. These were Δ-tetrahydrocannabinol (HPLC grade, >90%, ethanol solution), 2,6-dichloro-p-aminophenol, phenol, and 4-phenylphenol, (>98%, Sigma-Aldrich).

Solutions were prepared with deionized water of resistivity not less than 18.2 MOhm cm$^{-1}$ (Millipore Water Systems). Voltammetric measurements were carried out using a CH-650A potentiostat (CH Instruments, Austin, Tex.) with a three-electrode configuration. Glassy carbon electrodes (CH Instruments, Austin, Tex.) or carbon paste electrodes were used as working electrodes. Carbon paste was prepared from a mixture of 0.35 gram graphite and 0.1 gram Nujol oil, mixed by grinding in a mortar/pestle for 10-15 minutes. The carbon paste mixture was packed into a Teflon cylinder electrode case and contacted with a copper wire (CH Instruments, Austin, Tex.). The counter electrode was a bright platinum wire, with a saturated calomel or Ag/Ag$^+$ reference electrode completing the circuit. The glassy carbon electrodes were polished on silica lapping compounds (BDH) of decreasing sizes (0.1 to 0.05 um) on soft lapping pads, then rinsed with DI water immediately prior to use.

Electrochemical Experiments

All experiments were typically conducted at 20±2° C. Before commencing experiments, nitrogen was used for deaeration of solutions. Stock solutions of the substituted phenols were prepared by dissolving the required substituted phenol in methanol.

Figure 3:
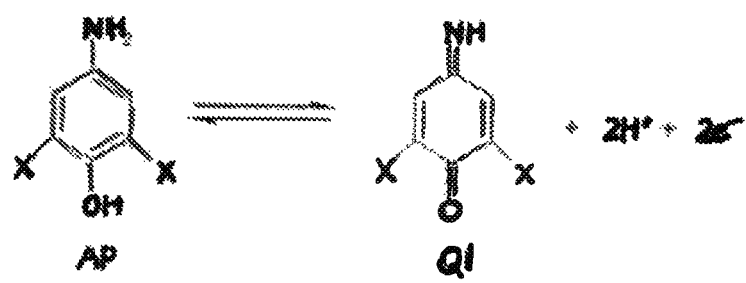
FIG. 3 is a chemical reaction showing an electrochemical oxidation of aminophenol.

Initial Voltammetric Characterization of 4-amino-2,6-dichlorophenol (PAP). First, the voltammetric response of a Glassy Carbon electrode in pH 10 borate buffer solution (50 mM) containing 1 mM 4-amino-2,6-dichlorophenol (PAP) was demonstrated. The corresponding voltammetry is shown in FIG. 4A. The oxidation peak is observed at +0.074 V (vs. Ag/Ag$^+$) with a corresponding reduction peak at +0.010V (vs. Ag/Ag$^+$) which is due to the redox system of p-aminophenol-quinoneimine (PAP-QI), FIG. 3.

The response of PAP to increasing additions of phenol was measured using square-wave voltammetry (SW-voltammetry) at a carbon electrode to try to increase the sensitivity of the protocol. SW-voltammetry was used because this technique has an increased sensitivity over linear sweep (or cyclic voltammetry), due to the fact that the former is a measure of the net current, which is the difference between the forward and reverse current pulses and also using SW-voltammetry, only one peak is observed, allowing one to easily monitor the reduction of the voltammetry peak on additions of the phenol compound.

Figure 5:
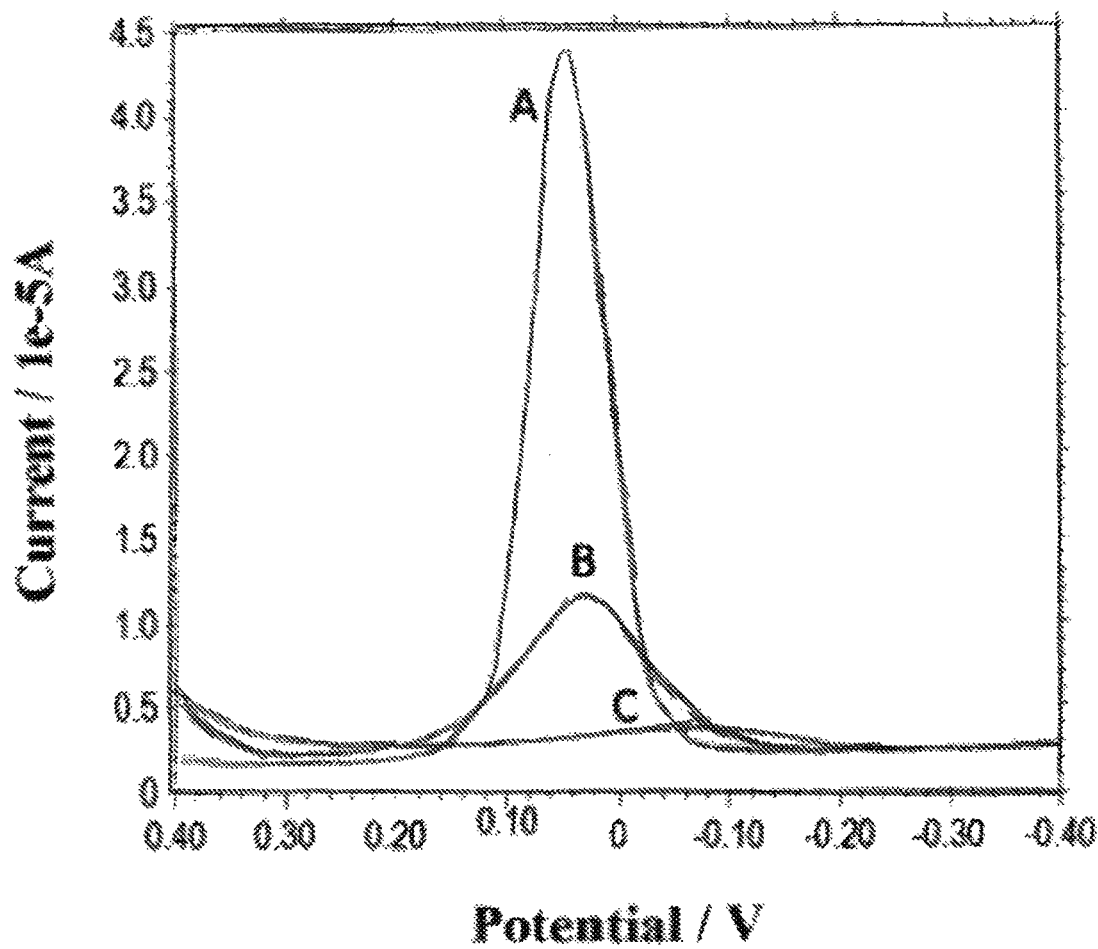
FIG. 5 is a graph showing a plurality of square wave voltammetric responses to PAP at a polished glassy carbon electrode.

Initially, the SW parameters were optimized. Using a pH 10 buffer solution containing 1 mM PAP, the frequency and step potential were each in turn changed to find the optimum peak height; this was consequently found to occur when the frequency was 8 Hz, the step potential 4 mV and the amplitude 25 mV. Using these parameters, the SW voltammetric response from a glassy carbon electrode was obtained in a pH 10 buffer solution containing 1 mM PAP. The voltammogram was cycled until the peak had stabilized, which is typically after two cycles, after which phenol additions were made to the solution. As depicted in FIG. 5, the SW voltammetric response to PAP at a polished glassy carbon electrode before (A) and after addition of 200 uM (B) and 400 uM (C) concentrations of p-phenlyphenol, where the signal is found to decrease with added phenol concentrations. The well-defined SW voltammetric response was found to decrease with added phenol concentrations. Chemical analysis of the peak current vs. added phenol concentration was found to be highly linear from 0 to 400 3M.

From this, a limit of detection (3σ) was found to be ~10 µM. Note that in employing SW voltammetry, which involves holding the potential at +0.4 V for 4 s, the direct oxidation of the phenol (or phenol derivatives) is completely avoided, such that any possible electrode passivation is circumvented. This explains the slightly less favorable regression data seen using cyclic voltammetry (in comparison to SW-voltammetry), where the potential is swept into the region where phenol oxidation occurs. Thus, given the simplicity and reduced possibility of electrode fouling from using the SW-voltammetry technique, this protocol was used throughout the following work.

A control experiment was performed where identical volume sized additions were made of either water or ethanol to a pH 10 borate buffer solution containing 1 mM PAP without any phenol present. No significant reduction in the PAP voltammetric peak was observed for both the water and ethanol additions. This indicates that neither dilution effects nor reaction with ethanol were responsible for the decrease in the voltammetric response of the PAP as observed in FIG. 5; thus, the latter is purely from the Gibbs reaction of phenol with QI.

Detection of Phenols in Aqueous Solutions at Carbon Paste Electrodes

Above, we have shown a useful electrochemical methodology for the indirect determination of substituted phenol compounds. We now turn to exploring if this protocol is able to detect THC at carbon paste electrodes. The chemical structure of the latter is shown in FIG. 1, where it can be seen that it is effectively a phenol derivative which should undergo attack from the electrochemically produced dichloro-benzoquinone monoamine.

Figure 4:
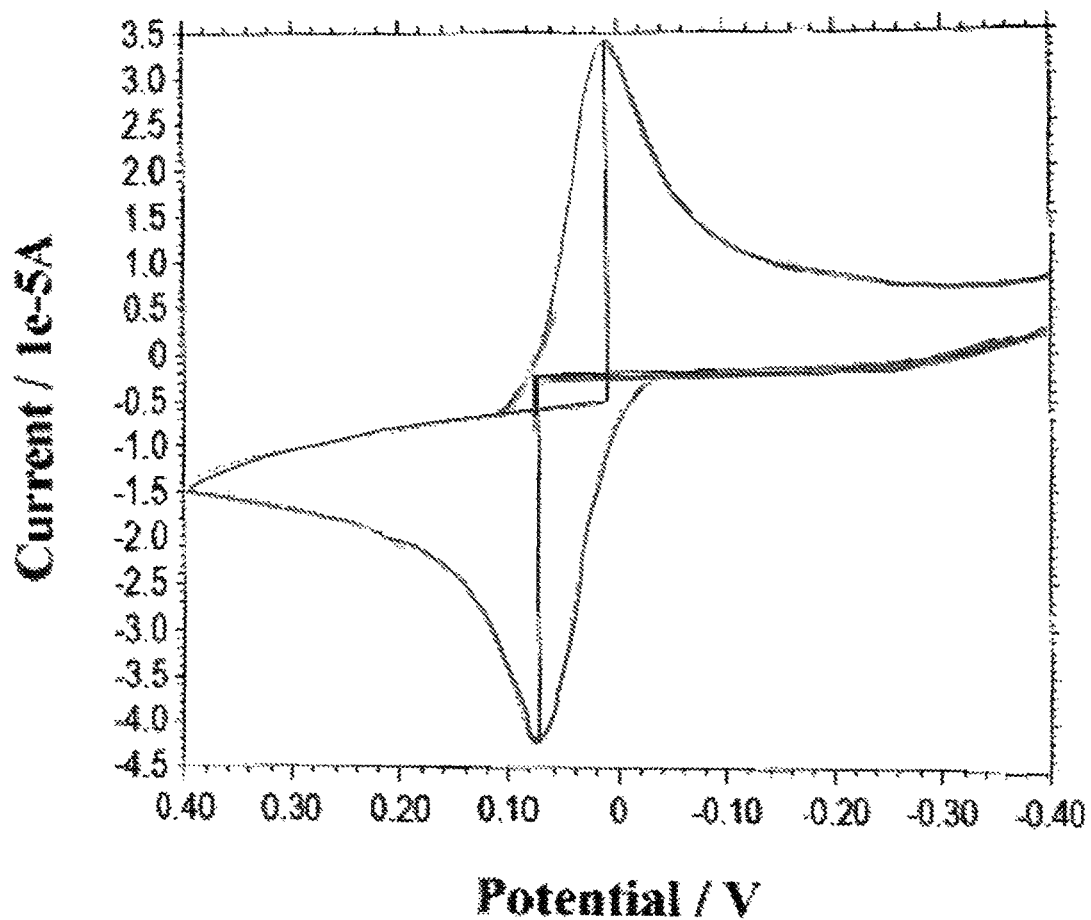
FIG. 4 is a graph showing cyclic voltammetry of 2,4 dichloro-p-aminophenol (PAP) in pH 10 borate buffer at 100 mV/s at a polished glassy carbon electrode.
Figure 6:
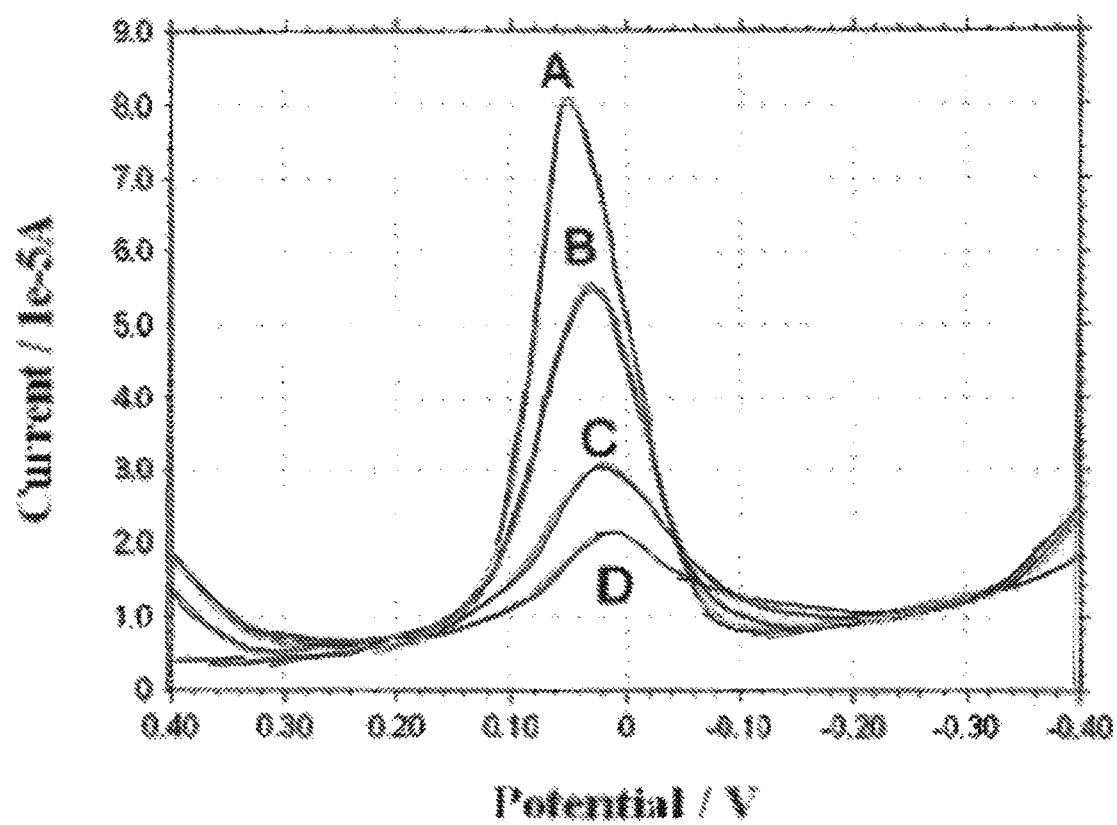
FIG. 6 is a graph showing a plurality of square wave voltammetric responses to PAP at a carbon paste electrode.

The electrochemical response at a glassy carbon electrode for the electrochemical oxidation of 1 mM PAP in a pH 10 borate buffer solution at 100 mV/s was established as shown in FIG. 4. Additions of phenol were made over the range of 100-600 µM to the solution, with the observed response depicted in FIG. 6. FIG. 6 shows the SW voltammetric response to PAP at a carbon paste electrode in pH 10 borate buffer before (A) and after addition of 200 uM (B), 400 uM (C) and 600 uM (D) concentrations of p-phenylphenol, where the signal is found to decrease with added p-phenylphenol concentrations. As observed for phenol additions described above, the reduction peak has decreased with increasing phenol additions, indicating that the protocol works as an indirect methodology for the detection of THC, the active part of *Cannabis*. We now turn to quantify this result with SW-voltammetry.

Figure 7:
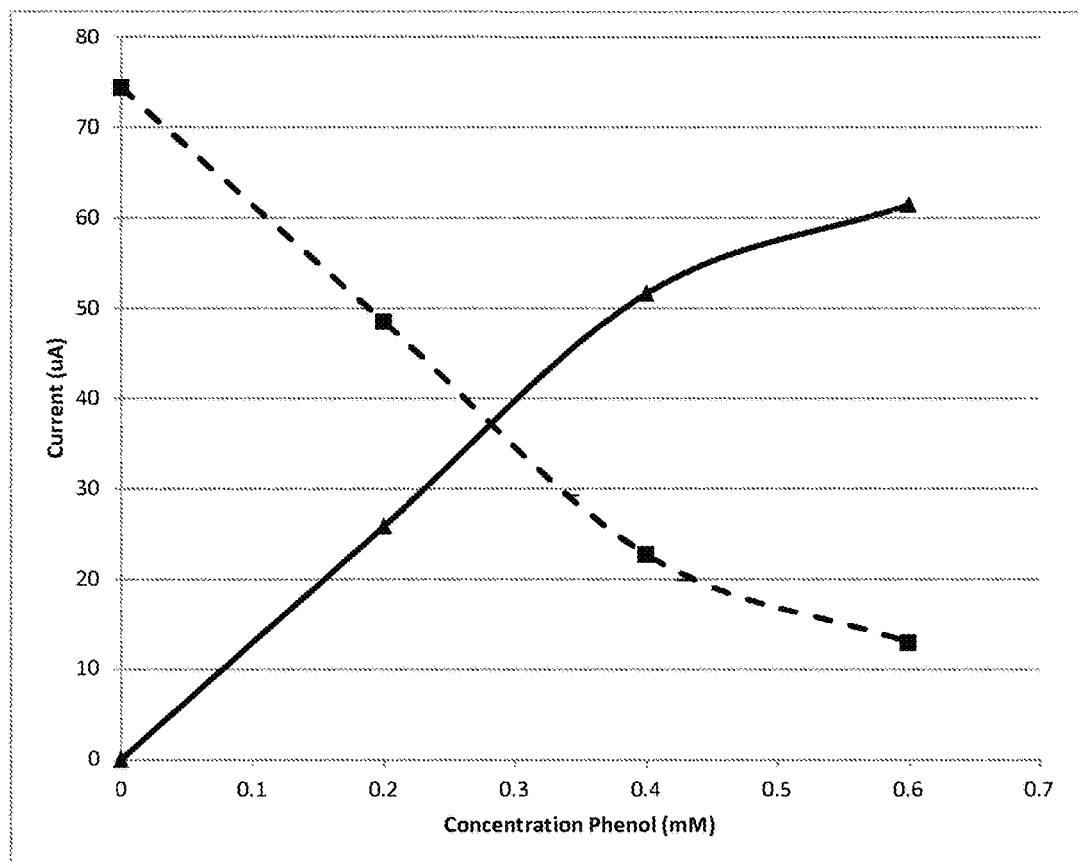
FIG. 7 is a graph of the peak height versus added phenol concentration for square wave voltammograms shown in FIG. 6.

Using a 1-mM PAP solution in a pH 10 borate buffer solution, additional SW-voltammetric responses were obtained using carbon paste electrodes. The response of additions of phenol was explored. As depicted in FIG. 7, the voltammetric peak was found to decrease with increasing additions of phenol. Chemical analysis of the peak height vs. added phenol concentrations revealed linear parts of the calibration curve. From this a limit of detection (3σ) was found to be 25 µM. While this limit of detection is not as low as previous analytical techniques (such as HPLC or gas chromatography as described in the introduction), these cannot be easily adapted to hand-held (portable) devices.

As indicated by the references cited, the detection of a variety of cannabinoid molecules should proceed in essentially the same manner. The phenolic part of the cannabinoid will undergo the same attack from the electrochemically produced dichloro-benzoquinone monoamine, and the concentration of the cannabinoid present can be inferred by the consumption of the electrochemically generated reagent. The strategy used for electrochemical detection can be selected from any of the widely known techniques, it was illustrated here with square wave voltammetry due to the convenience and availability of the instrumentation. Similar results should be obtained with a wide variety of electroanalytical techniques, including cyclic voltammetry, linear sweep voltammetry, normal pulse voltammetry, differential pulse voltammetry, chronoamperometry, chronocoulometry, sinusoidal voltammetry, ac impedance and other related methods.

Figure 8:
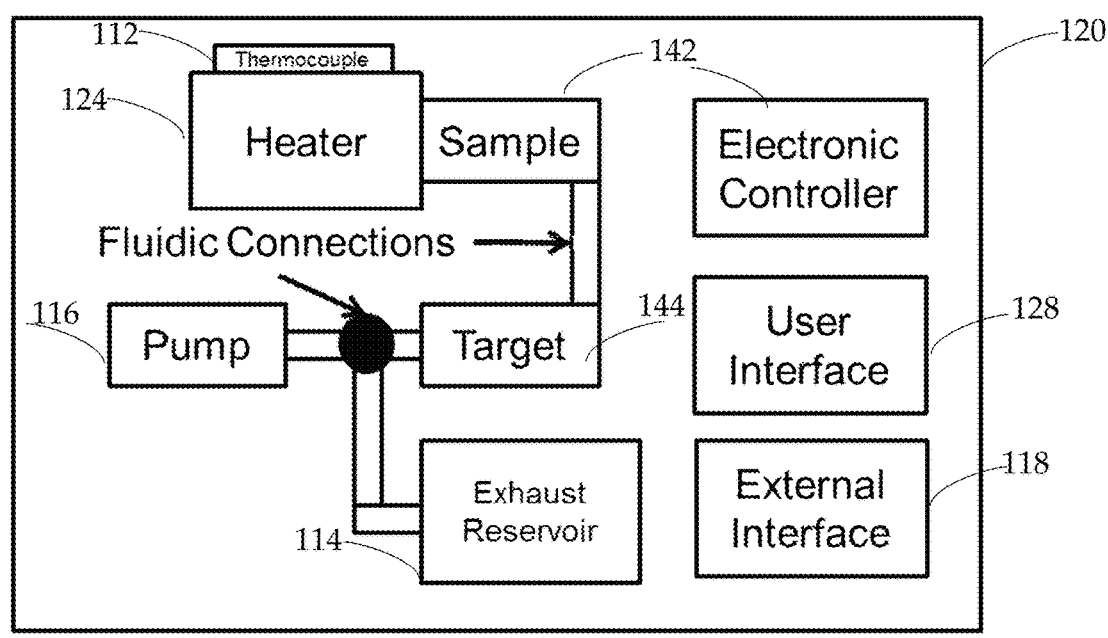
FIG. 8 is a block diagram of an example embodiment of a sampling instrument.

FIG. 8 show a schematic view of a sampling instrument assembly 120 in a gas fluidic system comprising an apparatus for releasing volatile elements of a substance comprising in combination a power supply with an electronic controller 128 in electrical communication with a heater 124 and a pump 116, a thermocouple 112 for sensing temperature, an user interface 122 and external interface 118 in electrical communication with the power supply, the electronic controller consisting in part, of a time and temperature control that adjusts the heat produced by the heater and length of time heat is produced, information output means in electrical communication with the power supply that displays the temperature and time, a sample 142 in a material holder which is insertable and removable for holding the substance connected via inert tubing to a target 144 in a target substrate holder which is insertable and removable for holding the target substrate. The time and temperature control means produces a variable heat according to the specific substance being volatized in the apparatus. In one configuration, a sampling device in which a syringe pump 116 pushes a sample gas from the heated sample chamber through a tube across a target substrate; once sampling is completed, the valve between the pump and the target chamber is closed and the syringe pump is refilled through an outlet.

Figure 12:
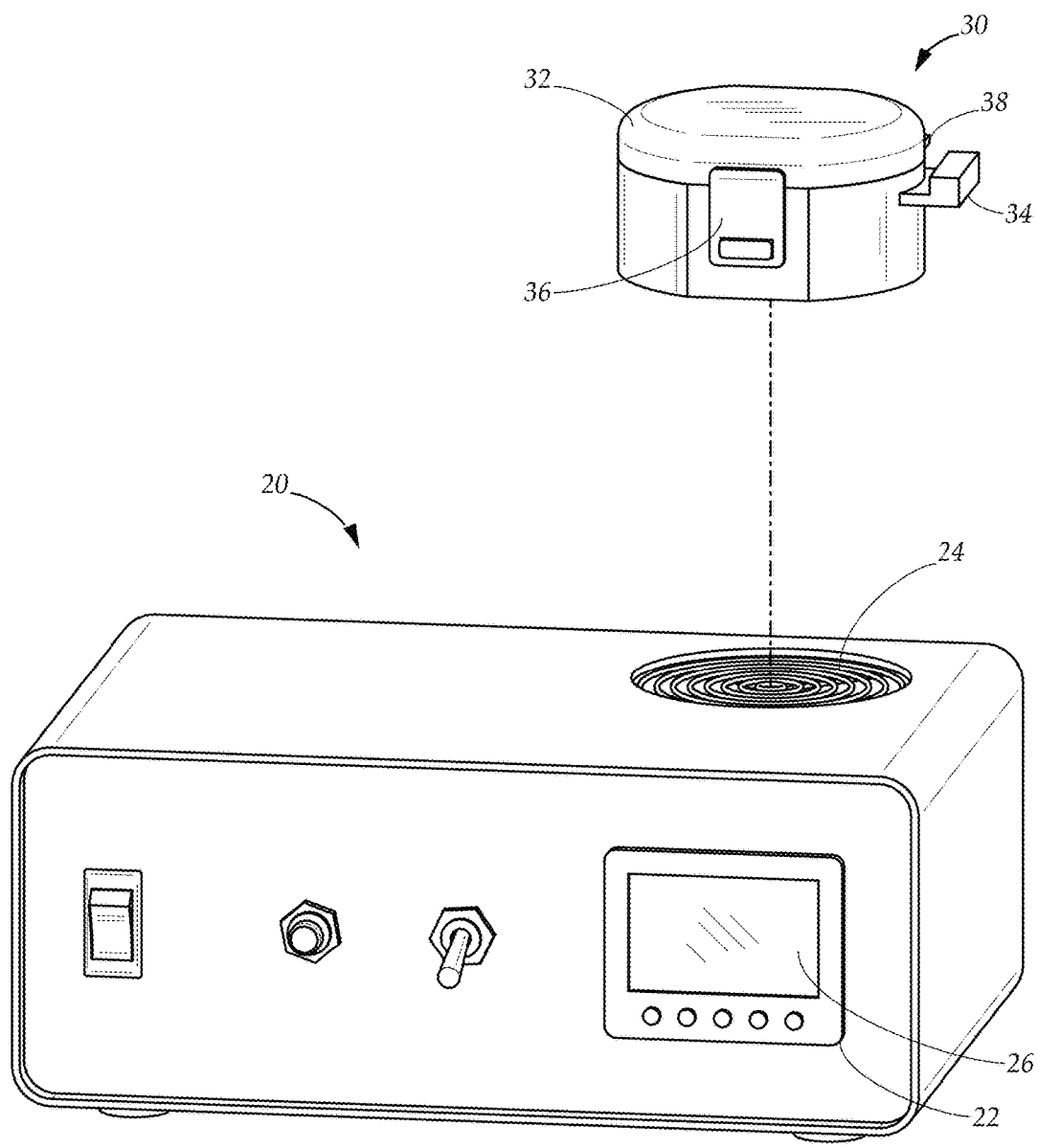
FIG. 12 is a perspective view of an example embodiment of the sampling device coupled to sampling instrument.

FIG. 12 shows the sampling instrument assembly 20 with the heater and pump below the grill 24. The sampling chamber 30 fits over the heater and pump. The sampling chamber has a seal 36 and a lid 32 to direct the sample gas over the analyte as discussed hereinbelow. The user interface 22 and display 26 allows the user to set the temperature and a heating mode, either isothermal or gradient heating. The target substrate holder 34 inserts into the sampling chamber 30 and as well as a sensor strip 38.

Figure 9:
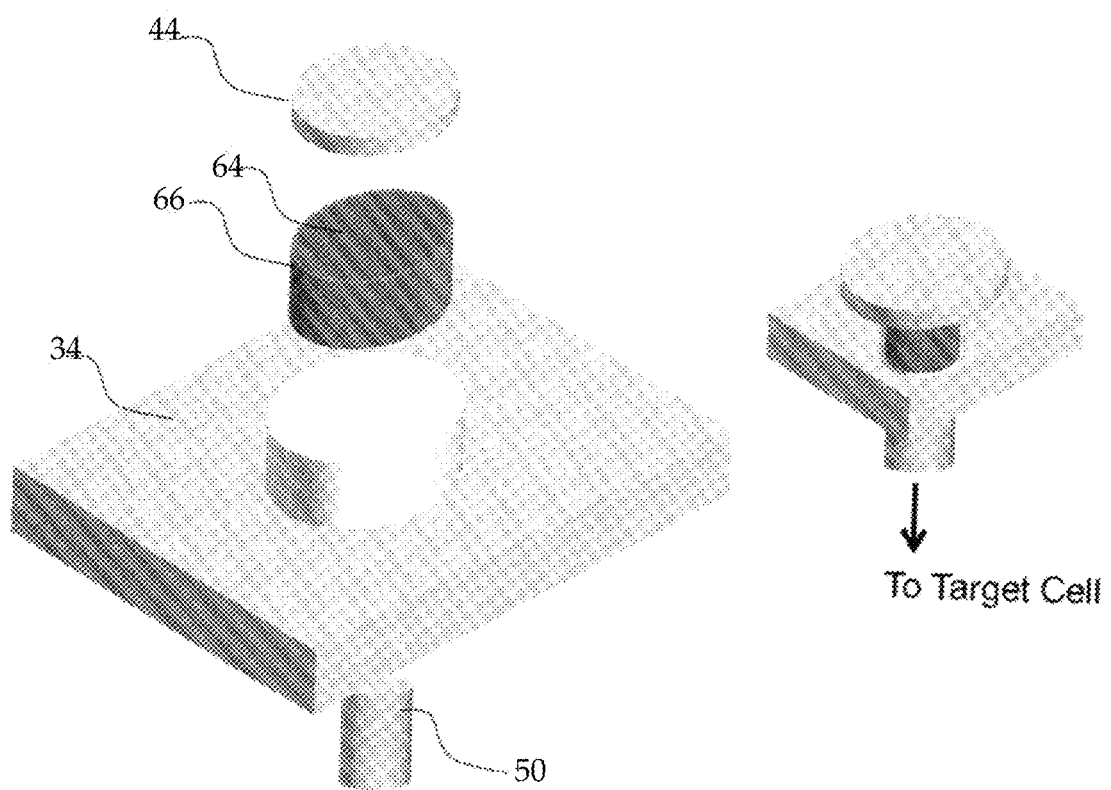
FIG. 9 is a schematic diagram of an example embodiment of a sampling device.

FIG. 9 shows a sampling cell 66 in which a pump pushes a sample gas 64 from a heated analyte in the heated sample chamber through a tube 50 across a target substrate 44 held in place on a target substrate holder 34; once sampling is completed, the valve between the pump and the target chamber is closed and the pump is refilled through an outlet. After the sample is drawn across the target substrate 44, the target substrate is removed from the target chamber and placed in contact with an electrochemical sensor 38. The electrochemical sensor and target substrate are placed in contact and a small volume of electrolyte provides sufficient conductivity and solubility of the target analytes, so as to allow measurement the composition of selected chemical species within the target substrate.

Figure 10:
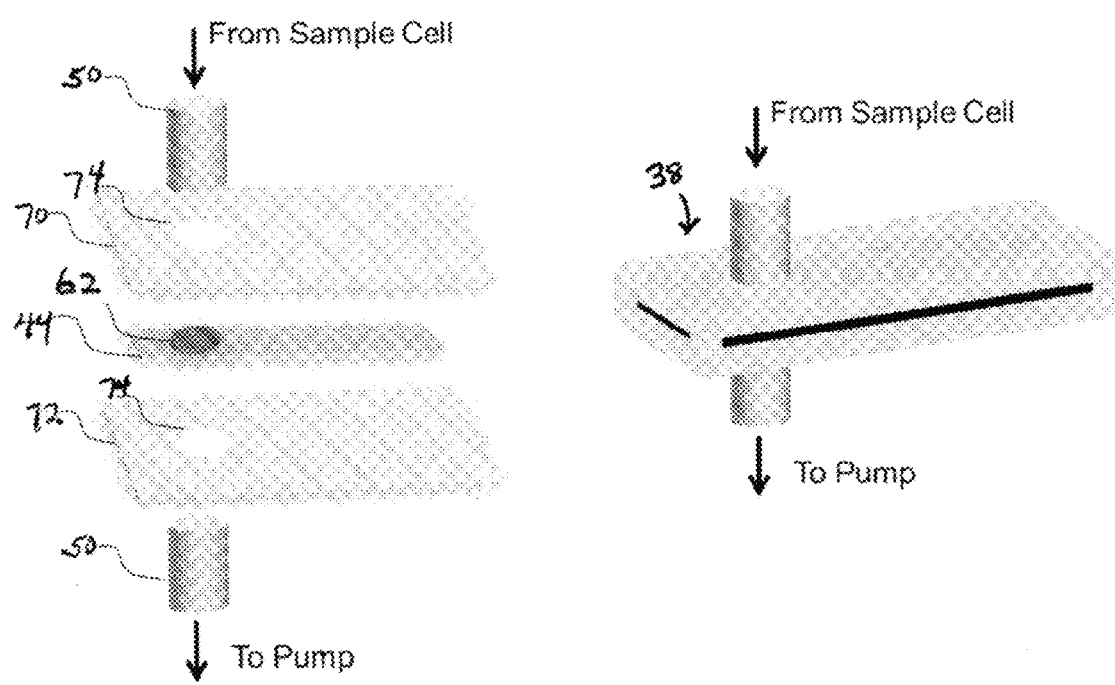
FIG. 10 is a schematic diagram of an example embodiment of a target holder.

FIG. 10 shows a target holder comprised of input 70 and output 72 sections, where the input section is connected to a sampling device via a hole 74 and a tubular connector 50 and the output device is connected to a pump via another hole 74 and additional tubular connector 50. The input and output sections surround a target substrate 44, onto which is deposited the volatilized components of the heated sample 62. This can be accomplished by pushing a sample gas into the heated sample chamber through target holder across a target substrate. The target substrate is comprises a solid support and/or adsorption matrix, configured to enhance the adsorption of selected sample vapors.

Figure 11:
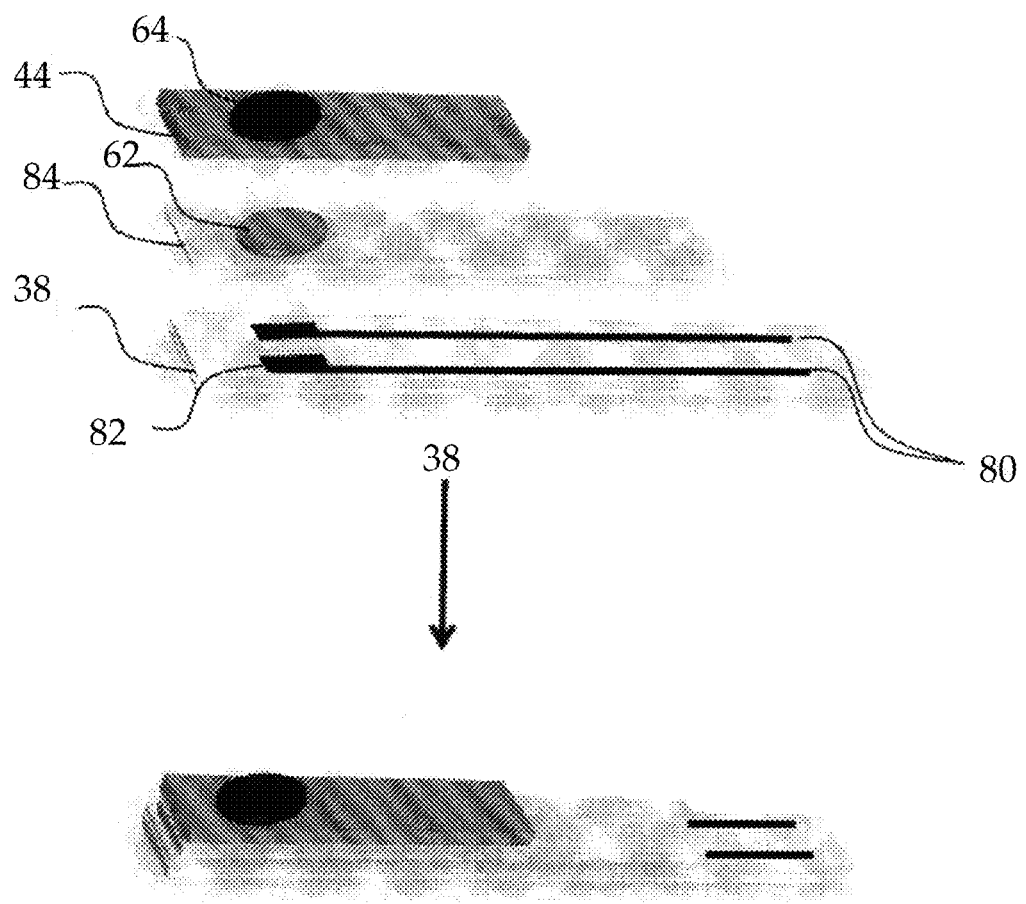
FIG. 11 is a schematic diagram of an example embodiment of an electrochemical sensor strip.

FIG. 11 shows a possible configuration of an electrochemical sensor stipr 38 designed for use with a vapor-deposited target. After the sample vapors are drawn across the target substrate 44 and the sample vapors are deposited on such substrate 44, the target substrate 44 is removed from the target chamber and placed in contact with a reagent strip 38 containing essential reagents 40 deposited within and an electrochemical sensor 38 containing electrodes 82 and connections 80. The electrochemical sensor, reagent strip and target substrate are placed in contact and a small volume of electrolyte provides sufficient conductivity and solubility of the reagents and target analytes, so as to allow electrochemical measurement the composition of selected chemical species within the target substrate via the separate sensor substrate. The essential reagents may include an electrolyte solution.

Figure 13:
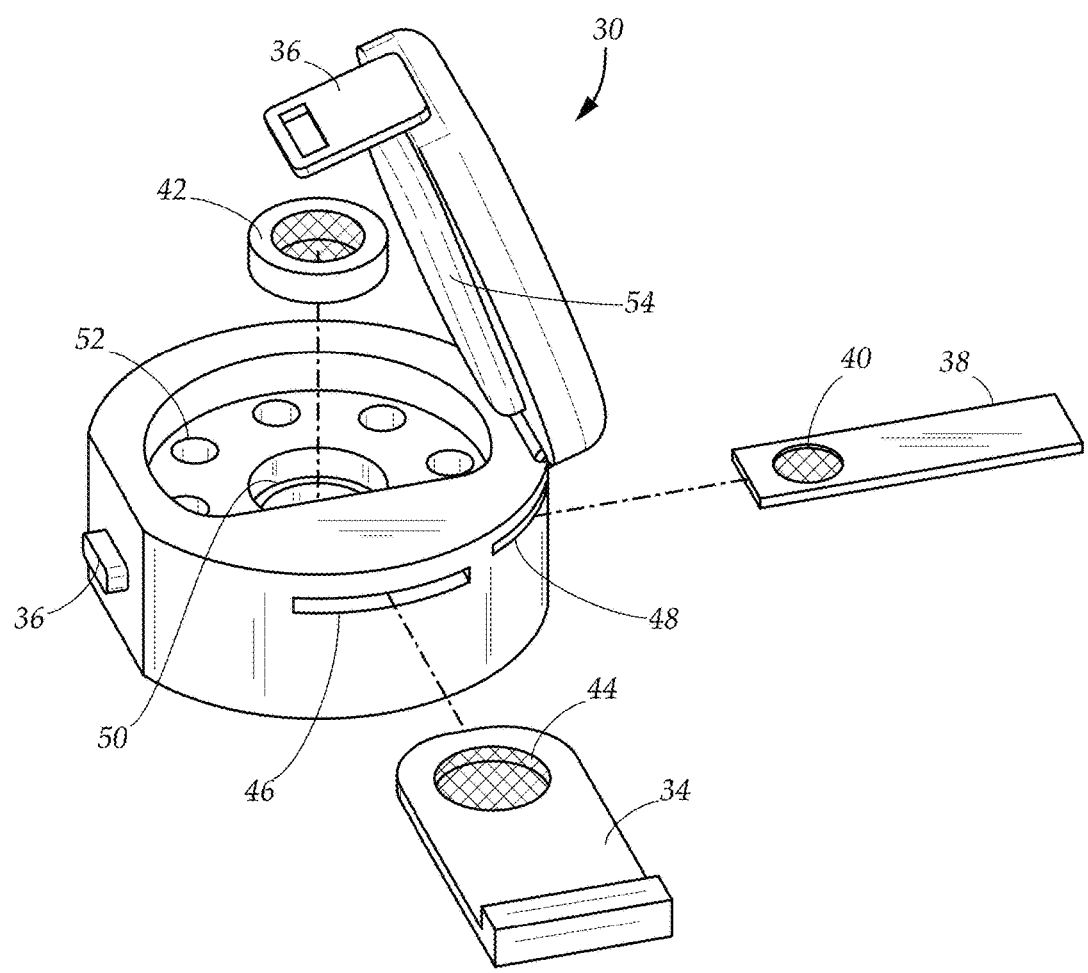
FIG. 13 is an exploded view of an example embodiment of the sampling device.
Figure 14:
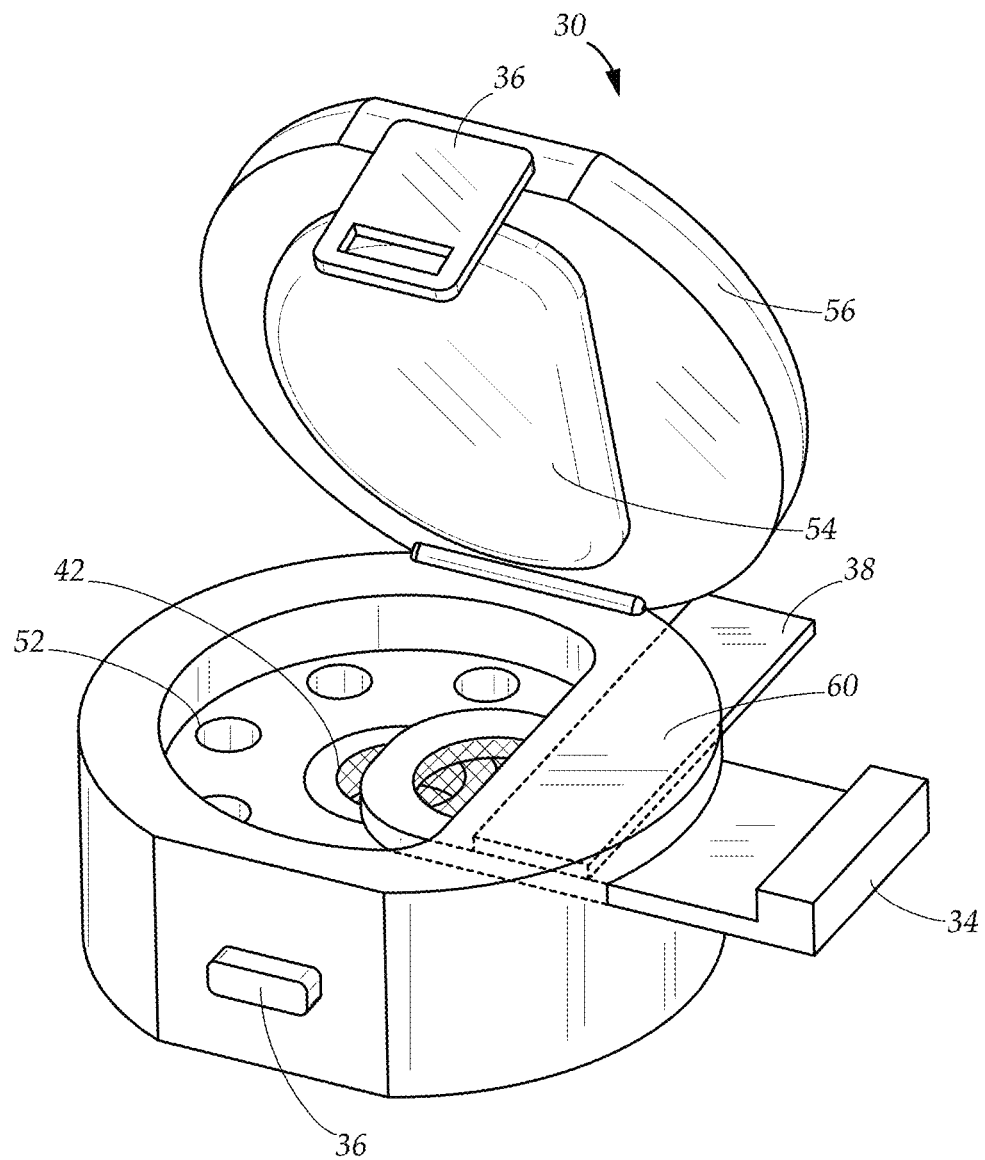
FIG. 14 is a perspective view of the example embodiment of the target holder, sample holder and electrochemical sensor strip disposed within an open sampling device.
Figure 15:
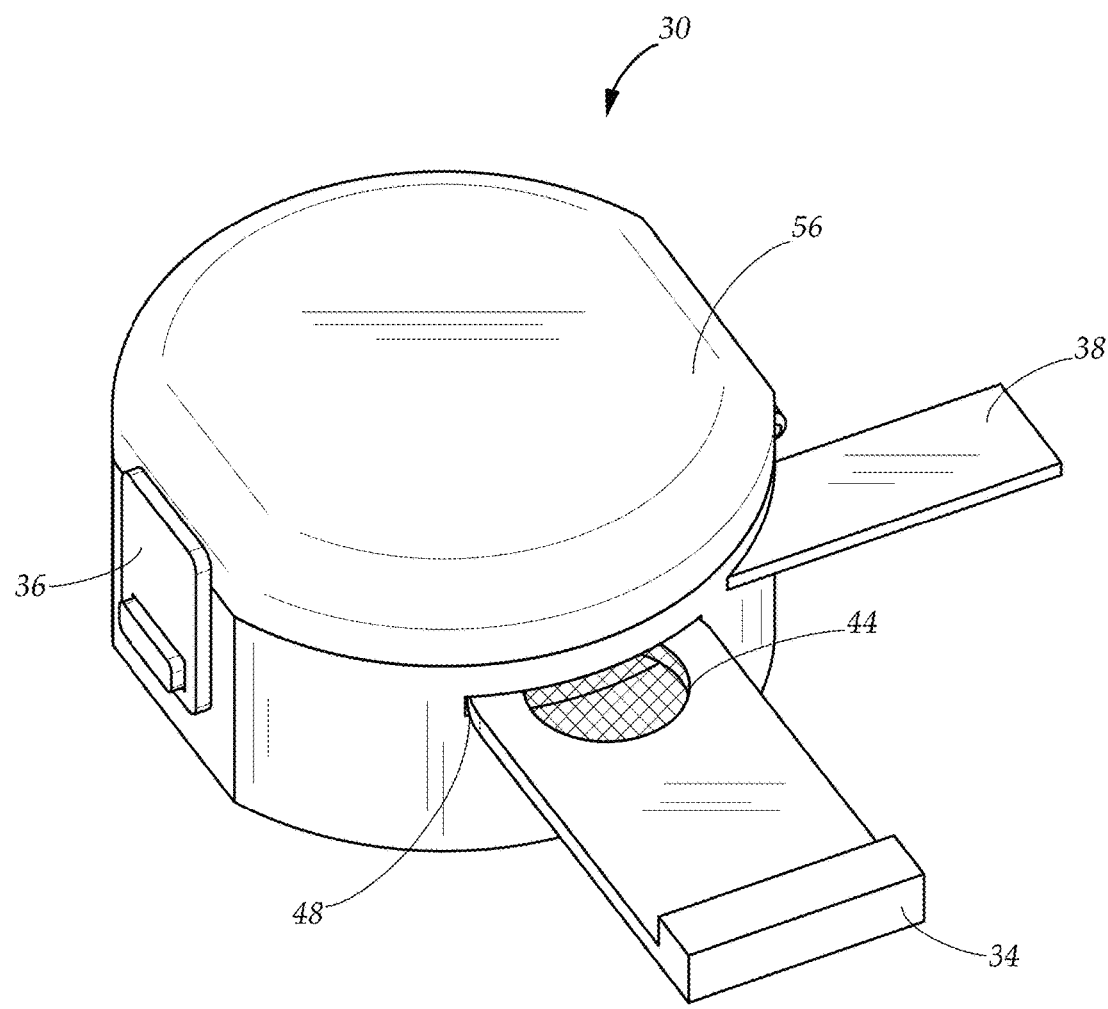
FIG. 15 is a perspective view the example embodiment of the target holder, and electrochemical sensor strip disposed within a closed sampling device.

FIGS. 13-15 illustrate the sampling chamber 30. The chamber has a lid 32 that has a seal 36 to maintain a closed chamber during the sampling process. The chamber has the tube 50 that extends to the sampling instrument of the gas fluidic system. A sample material holder 42 sits over the tube 50 to receive the heated gas from sampling instrument as described hereinabove. A plug 54 fits over the portion holding the sample material. A plurality of vents 52 is provided to prevent a backpressure increase.

The chamber has a first slot 48 and a second slot 46. A target substrate holder 34 with a target substrate 44 inserts into the second slot 46. A sensor strip 38 preferably with at least one reagent 40 is on the sensor strip. The reagent strip may be on a separate strip in fluid communication with the sensor strip. The sensor strip 38 inserts into the slot 46.

During the initial heating the target substrate holder 34 is fully inserted in the second slot 46, maintaining the target substrate 44 over the sample material holder 42. Once the at least one volatile component of the analyte in the sample material holder 42 is retained on the target substrate 44, the target substrate holder 34 is partially withdrawn so that the target substrate 44 is in contact with the sensor strip 38.

In one example embodiment, the sensor strip 38 measures the at least one volatile component directly when the sensor strip 38 is in electrical communication with a meter such as a potentiostat or other instruments that measure voltammetric response as described hereinabove. In another example embodiment, the sensor strip 38 is withdrawn and inserted into another analytical instrument for measurement, such as a meter or spectrophotometer.

Although the disclosure has been described and illustrated with a certain degree of particularity, it is understood that the present disclosure has been made only by way of example, and that numerous changes in the combination and arrangement of parts can be resorted to by those skilled in the art without departing from the spirit and scope of the disclosure, as hereinafter claimed.

It is understood that when an element is referred hereinabove as being "on" another element, it can be directly on the other element or intervening elements may be present therebetween. In contrast, when an element is referred to as being "directly on" another element, there are no intervening elements present.

Moreover, any components or materials can be formed from a same, structurally continuous piece or separately fabricated and connected.

It is further understood that, although ordinal terms, such as, "first," "second," "third," are used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

Spatially relative terms, such as "beneath," "below," "lower," "above," "upper" and the like, are used herein for ease of description to describe one element or feature's relationship to another element(s) or feature(s) as illustrated in the figures. It is understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device can be otherwise oriented (rotated 90 degrees or at other orientations) and the spatially relative descriptors used herein interpreted accordingly.

Example embodiments are described herein with reference to cross section illustrations that are schematic illustrations of idealized embodiments. As such, variations from the shapes of the illustrations as a result, for example, of manufacturing techniques and/or tolerances, are to be expected. Thus, example embodiments described herein should not be construed as limited to the particular shapes of regions as illustrated herein, but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

In conclusion, herein is presented instrumentation used in the collection of chemical samples from food and agricultural products, the chemical analysis of those samples and the disposition of the data collected in the chemical analysis of those samples. The disclosure is illustrated by example in the drawing figures, and throughout the written description. It should be understood that numerous variations are possible, while adhering to the inventive concept. Such variations are contemplated as being a part of the present disclosure.

What is claimed is:

1. A sampling chamber for selectively attaching to a gas fluidic system, comprising:
    a sample holder for maintaining an analyte having at least one volatile component, the sample holder in fluid communication with a gas fluidic system;
    a target substrate configured for collecting at least one volatile component from the analyte disposed in the sample holder;
    a sensor assembly configured for measuring the at least one volatile component from the analyte, the sensor assembly disposed within a first slot in the sampling chamber; and
    a target substrate holder within a second slot in the sampling chamber, the target substrate holder configured for maintaining the target substrate over the sample holder when retaining the at least one volatile component from the analyte and the target substrate be movable within the second slot into contact with the sensor assembly.

2. The sampling chamber as described in claim 1, wherein the sampling chamber has a tube connecting to the gas fluidic system such that a heated gas from the gas fluidic system travels through the sample holder.

3. The sampling chamber as described in claim 2, wherein the first slot maintaining the sensor assembly and the second slot maintaining the target substrate holder intersect within the sampling chamber such that the target substrate is in contact with the sensor assembly.

4. The sampling chamber as described in claim 3, wherein the sensor assembly measures the at least one volatile component from the analyte while maintained within the first slot of the sampling chamber.

5. The sampling chamber as described in claim 4, wherein the sensor assembly is an electrochemical sensor assembly.

6. The sampling chamber as described in claim 5, wherein the electrochemical sensor assembly has at least one working electrode, and at least one reference electrode and an electrolyte solution.

7. The sampling chamber as described in claim 6, wherein the sensor assembly has at least one connection in electrical communication with a voltammetric meter.

\* \* \* \* \*